United States Patent [19]
Grossman

[11] Patent Number: 6,037,126
[45] Date of Patent: Mar. 14, 2000

[54] COMPOSITIONS, METHODS, KITS AND APPARATUS FOR DETERMINING THE PRESENCE OR ABSENCE OF PROTEIN COMPONENT OF TELOMERASE ENZYME

[75] Inventor: Abraham Grossman, Pleasantville, N.Y.

[73] Assignee: InVitro Diagnostics, Inc.

[21] Appl. No.: 08/873,709

[22] Filed: Jun. 12, 1997

[51] Int. Cl.[7] .............................. C12Q 1/68; C12P 19/34; C07H 21/04
[52] U.S. Cl. ........................... 435/6; 435/7.1; 435/91.21; 435/91.3; 435/91.31; 435/91.32; 435/91.4; 435/91.41; 435/91.51; 435/91.52; 435/91.33; 435/194; 536/23.1; 536/23.72; 536/24.31; 536/25.3
[58] Field of Search .......................... 435/6, 91.2, 91.21, 435/91.3, 91.31, 91.32, 91.4, 9.41, 91.51, 91.52, 7.1, 194, 91.33; 536/23.1, 23.72, 24.31, 25.3

[56] References Cited

U.S. PATENT DOCUMENTS 5,583,016  12/1996  Villeponteau et al. ................. 435/91.3
5,759,773   6/1998  Tyagi et al. ................................. 435/6

*Primary Examiner*—Carla J. Myers
*Attorney, Agent, or Firm*—Anthony J. Janiuk

[57] ABSTRACT

The present invention is directed to methods, compositions, kits and apparatus to identify and detect the presence or absence of target analytes. The embodiments of the present invention have utility in identification of protein component of human telomerase and measurement of its levels in specimens and samples, as well as the design of test kits and apparatus for implementing such methods.

15 Claims, 10 Drawing Sheets

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
       (A) LENGTH: 444 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:1:

```
GGGUUGCGGA GGGUGGGCCU GGGAGGGGUG GGGCCAUUUU UUGUCUAACC CUAACUGAGA      60
AGGGCGUAGG CGCCGUGCUU UUGCUCCCCG CGCGCUGUUU UUCUCGCUGA CUUUCAGCGG     120
GCGGAAAAGC CUCGGCCUGC CGCCUUCCAC CGUUCAUUCU AGAGCAAACA AAAAAUGUCA     180
GCUGCUGGCC CGUUCGCCUC CCGGGGACCU GCGGCGGGUC GCCUGCCCAG CCCCCGAACC     240
CCGCCUGGAG CCGCGGUCGG CCCGGGGCUU CUCCGGAGGC ACCCACUGCC ACCGCGAAGA     300
GUUGGGCUCU GUCAGCCGCG GGUCUCUCGG GGGCGAGGGC GAGGUUCACC GUUUCAGGCC     360
GCAGGAAGAG GAACGGAGCG AGUCCCGCCG CGGCGCGAUU CCCUGAGCUG UGGGACGUGC     420
ACCCAGGACU CGGCUCACAC AUGC                                           444
```

(2) INFORMATION FOR SEQ ID NO:2:

(i) SEQUENCE CHARACTERISTICS:
       (A) LENGTH: 69 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:2:

```
GGGGACCCCC CCGGAAGGGG GGGACGAGGU GCGGGCACCU CGUACGGGAG UUCGACCGUG      60
ACGCUCUAG                                                             69
```

(2) INFORMATION FOR SEQ ID NO:3:

(i) SEQUENCE CHARACTERISTICS:
       (A) LENGTH: 166 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:3:

```
AGAUCUAGAG CACGGGCUAG CGCUUUCGCG CUCUCCCAGG UGACGCCUCG UGAAGAGGCG      60
CGACCUUCGU GCGUUUCGGU GACGCACGAG AACCGCCACG CUGCUUCGCA GCGUGGCUCC     120
UUCGCGCAGC CCGCUGCGCG AGGUGACCCC CCGAAGGGGG GUUCCC                    166
```

(2) INFORMATION FOR SEQ ID NO:4:

(i) SEQUENCE CHARACTERISTICS:
       (A) LENGTH: 37 base pairs
       (B) TYPE: nucleic acid
       (C) STRANDEDNESS: single (D) TOPOLOGY: linear (ii) MOLECULE TYPE: RNA (xi) SEQUENCE DESCRIPTION: SEQ ID NO:4:

GGGGAAAUCC UGUUACCAGG AUAACGGGGU UUCCUCA                                    37

(2) INFORMATION FOR SEQ ID NO:5:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:5:

CCUCUCUACU CGAAAGUUAG AGAGGACACA CCCGGAUCUA GCCGGGUCAA CCCA                 54

(2) INFORMATION FOR SEQ ID NO:6:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:6:

UACUGAGAA                                                                   9

(2) INFORMATION FOR SEQ ID NO:7:

(i) SEQUENCE CHARACTERISTICS:
            (A) LENGTH: 6 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:7:

UACCGA                                                                      6

(2) INFORMATION FOR SEQ ID NO:8:

(i) SEQUENCE CHARACTERISTICS:
            (A) LENGTH: 5 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:8:

GGGAA                                                                       5

(2) INFORMATION FOR SEQ ID NO:9:

(i) SEQUENCE CHARACTERISTICS:
            (A) LENGTH: 3 base pairs
            (B) TYPE: nucleic acid
            (C) STRANDEDNESS: single
            (D) TOPOLOGY: linear (ii) MOLECULE TYPE: RNA

```
        (xi) SEQUENCE DESCRIPTION: SEQ ID NO:9:

GGG                                                                        3

(2) INFORMATION FOR SEQ ID NO:10:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:10:

CGCGTTCGTC CTCACTCTCT TCCGCATCGC TGTCTGCGAG GGCCAGGGCC                     50

(2) INFORMATION FOR SEQ ID NO:11:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:11:

TCGAGGCCCT GGCCCTCGCA GACAGCGATG AGCTCCC                                   37

(2) INFORMATION FOR SEQ ID NO:12:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:12:

GGGAGCTCAT CGCTGTCTGC GAGGGCCAGG GCC                                       33

(2) INFORMATION FOR SEQ ID NO:13:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:13:

AAGAGAGTGA GGACGAACGC GC                                                   22

(2) INFORMATION FOR SEQ ID NO:14:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"
```

(xi) SEQUENCE DESCRIPTION: SEQ ID NO:14:

TCGAGCGCGT TCGTCCTCAC TCTCTT                                            26

(2) INFORMATION FOR SEQ ID NO:15:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:15:

GGGAAGAGAG UGAGGACGAA CGCGC                                             25

(2) INFORMATION FOR SEQ ID NO:16:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:16:

GGCCCUGGCC CUCGCAGACA GCGAUGAGCU                                        30

(2) INFORMATION FOR SEQ ID NO:17:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:17:

CGCGTTCGTC CTCACTCTCT TCCGCATCGC TGTCTGCGAG GGCCAGGGCC                  50

(2) INFORMATION FOR SEQ ID NO:18:

(i) SEQUENCE CHARACTERISTICS:
          (A) LENGTH: 54 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO:18:

GGCCCUGGCC CUCGCAGACA GCGAUGAGCU GGGAAGAGAG UGAGGACGAA CGCG             54

(2) INFORMATION FOR SEQ ID NO:19:

(i) SEQUENCE CHARACTERISTICS:
          (A) LENGTH: 66 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:19:

TCGAGGGGTT GCGGAGGGTG GGCCTGGGAG GGGTGGTGGC CATTTTTTGT CTAACCCTAC       60

(2) INFORMATION FOR SEQ ID NO:20:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
TTCTCAGTAG GGTTAGACAA AAAATGGCCA CCACCCCTCC CAGGCCCACC CTCCGCAACC    60

CC                                                                  62
```

(2) INFORMATION FOR SEQ ID NO:21:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
AAGAAGGGCG TAGGCGCCGT GCTTTTGCTC CCCGCGCGCT GTTTTTCTCG CTGACTTTCA    60

GCGGGCGGAA AAGCCTCGGC CTGCCGCCTT CGT                                93
```

(2) INFORMATION FOR SEQ ID NO:22:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
TCGAACGAAG GCGGCAGGCC GAGGCTTTTC CGCCCGCTGA AAGTCAGCGA GAAAAACAGC    60

GCGCGGGGAG CAAAAGCACG GCGCCTACGC CCTTCTT                            97
```

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:23:

```
CUAACCCUAC                                                          10
```

(2) INFORMATION FOR SEQ ID NO:24:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: other nucleic acid

```
         (A) DESCRIPTION: /desc = "promoter"

(xi) SEQUENCE DESCRIPTION: SEQ ID NO:24:

ATTATGCTGA GTGATATCCC CTTTAGGACA ATGGTCCTAT TGCCCCAAAG GAGACCCAAC        60

GCCTCCCACC CGGACCCTCC CCACCACCGG TAAAAAACAG ATTGGGATGA CT              112

(2) INFORMATION FOR SEQ ID NO:25:

(i) SEQUENCE CHARACTERISTICS:
         (A) LENGTH: 169 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "promoter"

(xi) SEQUENCE DESCRIPTION: SEQ ID NO:25:

ATTATGCTGA GTGATATCCC TTCCCGCATC CGCGGCACGA AAACGAGGGG CGCGCGACAA        60

AAAGAGCGAC TGAAAGTCGC CCGCCTTTTC GGAGCCGGCG CCTTTTCGGA GCCGGCCAGA       120

GATGACGTTT CAATCTCTCC TGTGTGGGCC TAGATCGGCC CAGTTGGGT                   169
```

COMPOSITIONS, METHODS, KITS AND APPARATUS FOR DETERMINING THE PRESENCE OR ABSENCE OF PROTEIN COMPONENT OF TELOMERASE ENZYME

FIELD OF THE INVENTION

The present invention is directed to methods, compositions, kits and apparatus to identify and detect the presence or absence of the enzyme, telomerase. The embodiments of the present invention have utility in the identification of the protein component of human telomerase and measurement of its levels in specimens and samples.

BACKGROUND OF THE INVENTION

The enzyme, telomerase, appears active in nearly all tumors. Telomerase activity is a potential marker for the development of malignant tumors (Nelson, 1996). Telomerase activity is most frequently detected by the PCR based Telomeric Repeat Amplification Protocol (TRAP) developed by Kim et al., (1994). However, the original TRAP assay had several limitations. The assay is laborious and time-consuming. The original assay used radioisotope labeling techniques. Such techniques require special laboratory precautions. The assay is difficult to quantify due to the assay's non-linearity. The inhibition of Taq polymerase activity by cellular components in clinical specimens may lead to the false negative results. The assay requires special preparation and preservation of the specimens. Finally, the assay is difficult to automate. The TRAP assay has been modified to achieve better sensitivity, eliminate the hazardous radioactive labeling and represent results in a semi-quantitative mode (Wright et al., 1995, Ohyashiki et al., 1996).

The molecular structure of human telomerase is believed to be similar to the enzyme of other organisms. The enzyme derived from Tetrahymena is believed to be composed of a first protein subunit (p80), a second protein subunit (p95), and a telomerase RNA molecule. The two protein subunits are bound each other and at the same time manifest a specific affinity to nucleic acid sequences. The first subunit binds telomerase's RNA component with high affinity and specificity. The second subunit binds the telomeric DNA primer sites. As used herein, the term "first subunit" refers to such subunit which binds the RNA component, even though such subunit may have a molecular weight other than 80 kilodaltons. Similarly, the term "second subunit" refers to such subunit which binds the telomeric DNA, even though such subunit may have a molecular weight other than 95 kilodaltons. These two proteins and two nucleic acid components form an RNP complex. The RNP complex is stable and at the same time accesible for a synthesis of the telomere DNA in the region where such synthesis actually is occurring (Collins et al., 1995).

Human telomerase RNA, hTR, is composed of 445 nucleotides. The sequence is set forth in Seq. ID No 1 below:

```
5'-GGGUUGCGGA GGGUGGGCCU GGGAGGGGUG GUGGCCAUUU      Seq ID No. 1

UUUGUCUAAC CCUAACUGAG AAGGGCGUAG GCGCCGUGCU UUUGCUCCCC

GCGCGCUGUU UUUCUCGCUG ACUUUCAGCG GGCGGAAAAG

CCUCGGCCUG CCGCCUUCCA CCGUUCAUUC UAGAGCAAAC AAAAAAUGUC

AGCUGCUGGC CCGUUCGCCU CCCGGGGACC UGCGGCGGGU CGCCUGCCCA

GCCCCCGAAC CCCGCCUGGA GCCGCGGUCG GCCCGGGGCU UCUCCGGAGG

CACCCACUGC CACCGCGAAG AGUUGGGCUC UGUCAGCCGC GGGUCUCUCG

GGGGCGAGGG CGAGGUUCAC CGUUUCAGGC CGCAGGAAGA

GGAACGGAGC GAGUCCCGCC GCGGCGCGAU UCCCUGAGCU GUGGGACGUG

CACCCAGGAC UCGGCUCACA CAUGC-3'
```

(Feng et al., 1995, Zaug et al., 1996).

A need exists for improved diagnostic and analytical methods to detect the presence or absence of telomerase and to measure the levels of enzyme activity in clinical samples and specimens. Such an assay has utility in the diagnosis of various cancers and identification of metastasises. A need also exists to detect telomerase enzyme with the analytical methods of nucleic acid chemistry. Furthermore, a need exists to develop a telomerase detection assay that does not require expensive equipment, large laboratory facilities or highly trained technical personnel. Ideally, a test will be inexpensive, non-labor-intensive and capable of automation.

SUMMARY OF INVENTION

The present invention features methods, compositions, kits, and apparatus for determining the presence or absence of the first subunit protein component of a telomerase molecule.

One embodiment of the present invention is a composition. The composition comprises a first ribonucleic acid (RNA) molecule and a second RNA molecule. The first RNA molecule is capable of binding to a first subunit protein molecule and has the following formula:

$$5'—A—B—C—3'$$

As used above, the letter "A" represents a section of the RNA molecule having 10–100,000 nucleotides, which section can be received by an RNA replicase and with another RNA sequence, F, being replicated. The letter "B" denotes a section of the RNA molecule having approximately 10 to 250 nucleotides in a first sequence having an affinity to at least one subunit protein component of telomerase, which section is capable of binding to such subunit protein molecule. The letter "C" denotes a section of the RNA molecule having approximately 1 to 10,000 nucleotides which section is capable of being ligated to another RNA sequence, "D". The second RNA molecule is capable of binding to a first subunit protein component and has the following formula:

As used above, the letter "D" is a section of the RNA molecule having approximately 1 to 10,000 nucleotides, which section is capable of being ligated to another RNA sequence, "C". The letter "E" denotes a section of the RNA molecule having approximately 10 to 250 nucleotides in a second sequence having an affinity to the subunit protein component of telomerase to which the section B exhibits affinity, which section E is capable of binding to such subunit protein component molecule. The letter "F" denotes a section of the RNA molecule having 10–100,000 nucleotides which section is capable of being received by an RNA replicase and with another sequence, "A", being replicated. The first and the second RNA molecules are capable of forming a third RNA molecule having the following formula:

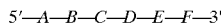

The third RNA molecule is formed by ligating the C and D sections, as the E and the B sections are bound to the subunit protein component. The third RNA molecule is capable of being received by an RNA replicase and being replicated by such enzyme.

The sequences represented by the letters A, B, C, D, E, and F may further comprise sequences and nucleotides which are artifacts of cloning or synthesis.

Preferably, the sequences represented by the letters "A" and "F" are selected from the group of sequences consisting of any Q-beta RNA template. RNA sequences which can be serve as a template comprise, by way of example, without limitation, microvariant RNA, nanovariant RNA, midivariant RNA and modifications of such sequences that maintain the ability of the sequences to be replicated by RNA replicase. Preferably, the replicase is Q-beta replicase.

Preferably, the sections B and E each are sections having 10–250 nucleotides and, even more preferred, nucleotides having a sequence of the RNA component of a telomerase molecule or non-naturally occurring RNA sequences that have affinity to the first or the second subunit protein component of telomerase. A preferred subunit protein component is the first subunit component. A preferred telomerase is human telomerase. Preferably, the sections B and E bind to the subunit protein component through non-nucleic acid base pairing interactions. And, most preferred, the B and E sections are selected for a particular functionality, such as binding to certain regions of the subunit protein component.

Preferably, the sequence of the section B is selected from the group of sequences from one region or one domain of a single region of the hTR molecule. The whole hTR molecule can be divided into three regions. One region is a long, branched stem, referred herein as the W region. Another region is a simple stem, referred herein as the X region. And, a third region, referred herein as the Y region, consists of two domains, referred herein as Y-1 and Y-2. The Y-1 domain, contains the telomerase template sequence, CUAACCCUAA, underlined in sequences above. Each of these hTR's regions has a unique secondary structure-- combinations of features (bulges and loops) conserved by double stranded stems. The sequence of the section E is preferably selected from the same group of regions and domains as B; however, the section E is different from section B.

The interaction of the sections B and E with a protein ligand, and the first subunit protein component, in particular, in some respects, is similar to nucleic acid probe-nucleic acid analyte hybridization.

Preferably, each section C and D has 1–10,000 nucleotides, and more preferred, 1–1000 nucleotides, and most preferred, 1–15 nucleotides.

A further embodiment of the present invention features a method of determining the presence or absence of at least one subunit protein component molecule. The method comprises the steps of providing a first RNA molecule and a second RNA molecule. The first RNA molecule is capable of binding to at least one subunit protein component molecule and has the formula

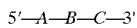

The sections A, B and C are as previously described. The second RNA molecule is capable of binding to the same subunit protein component molecule as the first RNA molecule and has the formula:

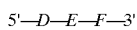

The sections D, E and F are as previously described. The method further comprises the step of imposing binding conditions on a sample potentially containing one or more of the subunit protein component molecules in the presence of the first and second RNA molecules. In the presence of the subunit protein component molecule, the first and the second RNA molecules form a ternary complex with such subunit protein component molecule. The method further comprises the step of imposing RNA ligase reaction conditions on the sample to form a third RNA molecule in the presence of the first subunit protein component molecule. The third RNA molecule has the formula:

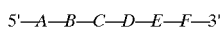

The sample is monitored for the presence of the third RNA molecule, the presence or absence of which is indicative of the presence or absence of a first subunit protein component molecule.

Preferably, the sections B and E each are sections having 10–250 nucleotides and, even more preferred, nucleotides having a sequence of RNA component of a telomerase molecule or nucleotides having a sequence that have affinity to one of the subunit protein components of telomerase. Preferably, the telomerase is human telomerase. Preferably, the sections B and E bind to the first subunit protein component through non-nucleic acid base pairing interactions. And, most preferred, the B and E sections are selected for a particular functionality, such as binding to certain regions of the first subunit protein component molecules. Preferably, the sequence of the section B is selected from the group of sequences from one region or one domain of a single region of the hTR molecule. The regions consist of the W, X, and Y regions. The domains consist of the Y-1 and Y-2 domains. The sequence of the section E is preferably selected from the group of regions and domains from which B is selected; however, the region or domain of E is different from section B.

Preferably, at least one of the first or second RNA molecules has a signal generating moiety. As used herein, a signal generating moiety refers to a sequence, ligand, enzyme, or chemical entity capable of being detected. By way of example, without limitation, such ligand may comprise an antibody or antigen, biotin or avidin or streptavidin, or a sequence capable or binding to a probe or forming an amplification product. In the presence of the enzyme Q-beta replicase, sequences recognized by the enzyme generate an amplification product.

After RNA ligase reaction conditions are imposed, the method preferably comprises the further step of separating or enzymatically destroying the RNA molecules unbound with the first subunit protein component molecule and bearing the signal generating moiety.

Preferably, the signal-generating moiety is sections A and F of the third RNA molecule, which sections allow recognition and replication by RNA replicase. Thus, the method further comprises the step of imposing RNA replicase conditions on the sample potentially comprising the third RNA molecule. Preferably the step of degrading the unbound RNA molecules is performed in the presence of the enzyme reverse transcriptase. Preferably, the step of amplifying the bound RNA molecules is performed in the presence of the enzyme Q-beta replicase.

An embodiment of the present invention further comprises a method of making a first RNA molecule and a second RNA molecule, wherein the first RNA molecule has the formula:

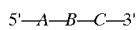

and the second RNA molecule has the formula:

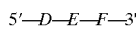

As used above, the letters A, B, C, D, E, and F are as previously described.

The method comprises the steps of providing a first DNA and a second DNA. The first DNA encodes the first RNA molecule and the second DNA encodes the second RNA molecule. The method farther comprises the step of transcribing the first DNA and the second DNA to form the first RNA molecule and the second RNA molecule.

Preferably, the first DNA and the second DNA are provided as sets of complementary oligonucleotides (dsDNA). The sets of first and second DNAs can be multiplied in plasmids when provided with suitable restriction sites and transcription sequences.

Preferably, a first starting dsDNA is made having a formula:

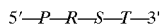

And, a second starting dsDNA is made having a formula:

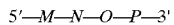

As used above, the letter "O" represents a DNA sequence encoding E and the letter "R" represents a DNA sequence encoding B. The letters "M," "P" and "T" represent restriction site linkers. The letter "N" represents a nucleotide sequence that encodes the section D of the second RNA molecule. The letter "S" represents a nucleotide sequence that encodes the section C of the first RNA molecule. The first and the second starting dsDNAs are joined with sequences of a Q-beta template insert using M and P restriction sites for the first starting dsDNA, and P and T restriction sites for the second starting dsDNA. The Q-beta template insert is carried as an insert in a recombinant first plasmid.

The organization of the insert in the first recombinant plasmid is:

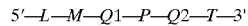

The letters "M", "P" and "T" represent the restriction sites for cloning the first and second dsDNAs. The letter "L" represents T7 RNA promoter sequence, the site of the promoter of RNA transcription. The letter "QI" represents sequences which encode a part of a Q-beta replicase template which correspond to section A of the first RNA molecule. The letter "Q2" represents sequences which encode a part of a Q-beta replicase template which correspond to the section F of the second RNA molecule.

The first recombinant plasmid having the dsDNA insert ecoded Q-beta replicase template is used to transform competent bacterial cells. The cells are cultured, harvested and the dsDNA of the first recombinant plasmid isolated. The first plasmid's DNA is subjected to restriction enzyme digestion and recombination with the first starting DNA and the second starting DNA to form a second recombinant plasmid and a third recombinant plasmid. The organization of the dsDNA of the second recombinant plasmid containing one embodiment of the second dsDNA is set forth below:

The second recombinant plasmid containing this second starting dsDNA is used to transform competent bacterial cells. The cells are cultured, harvested and the second recombinant plasmid dsDNA isolated.

The organization of the dsDNA of the third recombinant plasmid containing one embodiment of the first dsDNA is set forth below.

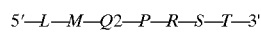

The third recombinant plasmid containing the first starting dsDNA is used to transform competent bacterial cells. The cells are cultured, harvested and the third recombinant plasmid dsDNA isolated.

The organization and composition of the recombinant RNA transcribed from the second recombinant plasmid (with the second starting dsDNA) after digestion with T restriction enzyme and using T7 RNA promoter and T7 RNA polymerase is:

The organization and composition of the recombinant RNA transcribed from the third recombinant plasmid (with the first starting dsDNA) after digestion with T restriction enzyme and using T7 RNA promoter and T7 RNA polymerase is:

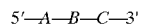

The letters A, B, C, D, E, and F are as previously described.

A further embodiment of the present invention comprises a method for construction of the first and the second RNA molecules omitting the cloning of starting dsDNAs in the first recombinant plasmid. The first and second RNA molecules will be directly transcribed from machine-synthesized first complementary DNA (cDNA) encoding the first RNA molecule and a machine synthesized second cDNA encoding the second RNA molecule.

The composition of the first cDNA representing the first recombinant RNA is:

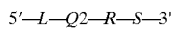

And, the composition of the second cDNA representing the second recombinant RNA is:

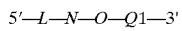

Wherein the sections represented by the letters L, N, O, Q1, Q2, R, and S are as previously described.

The organization and composition of the first recombinant RNA transcribed from the first synthesized cDNA molecules using T7 RNA promoter and T7 RNA polymerase is:

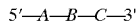

And, the organization and composition of the recombinant RNA transcribed from the second cDNA using T7 RNA promoter and T7 RNA polymerase is:

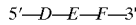

The letters A, B, C, D, E, and F are as previously described. These two recombinant RNA transcripts are the first and the second RNA molecules.

A further embodiment of the present invention comprises a kit for determining the presence or absence of a subunit protein component molecule. The kit comprises one or more reagents comprising a first RNA molecule and a second RNA molecule. The first RNA molecule has the formula:

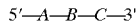

The second RNA molecule has the formula:

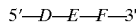

In the presence of a subunit protein component molecule, the first and the second RNA molecules are capable of forming a subunit-first-and-second-RNA ternary complex and in the presence of RNA ligase means forming a third RNA molecule having the formula:

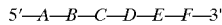

The letters A, B, C, D, E, and F are as previously described. The third RNA molecule is preferably capable of being received and replicated by RNA replicase.

Preferably, the kit further comprises other reagents, such as, RNA ligase, reverse transcriptase, suitable primers, buffers, intercalating agents and the like. As used herein the term "kit" refers to an assembly of parts, compositions and reagents with suitable packaging materials and instructions.

The present invention is further described in the following figure and examples, which illustrate features and highlight preferred embodiments and the best mode to make and use the invention.

DETAILED DESCRIPTION OF INVENTION

The present invention features methods, compositions, kits, and apparatus for determining the presence or absence of one of the subunit protein components of a telomerase molecule. The discussion which follows is directed to human telomerase with the understanding that the teaching would apply to the telomerase enzymes derived from other species as well. Further, the discussion features the methods, compositions, kits and apparatus for the detection of the first subunit protein component. RNA molecules with affinity to the second subunit protein component can be identified in accordance with the teaching of Gold et al (1995).

Surprisingly and unexpectedly, the most stable secondary structure of hTR contains several stem regions with intra-strand complementarity, which are interrupted by many symmetrical and asymmetrical bulges. FIG. I depicts the features of such secondary structure. The whole hTR molecule can be divided into three regions. One region is a long, branched stem, referred herein as the W region. This region consists of approximately the nucleotides 149 to and including 375 of SEQ ID No. 1.

Another region is a simple stem, referred herein as the X region. This region consists of approximately the nucleotides 378 to and including 445 of SEQ ID No. 1.

Figure 1:
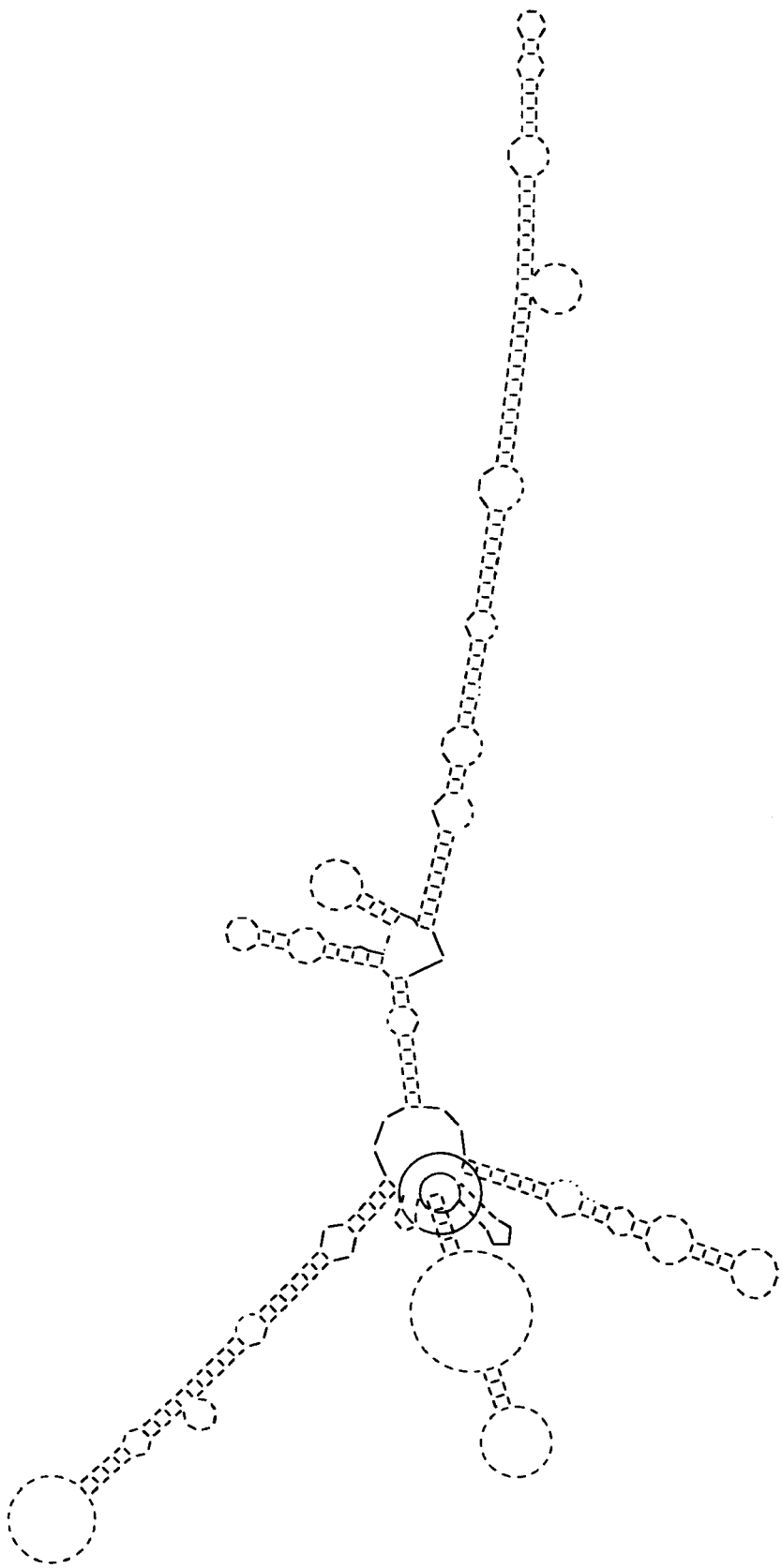
FIG. 1 depicts the secondary structure of human telomerase RNA- hTR.
Figure 2A:
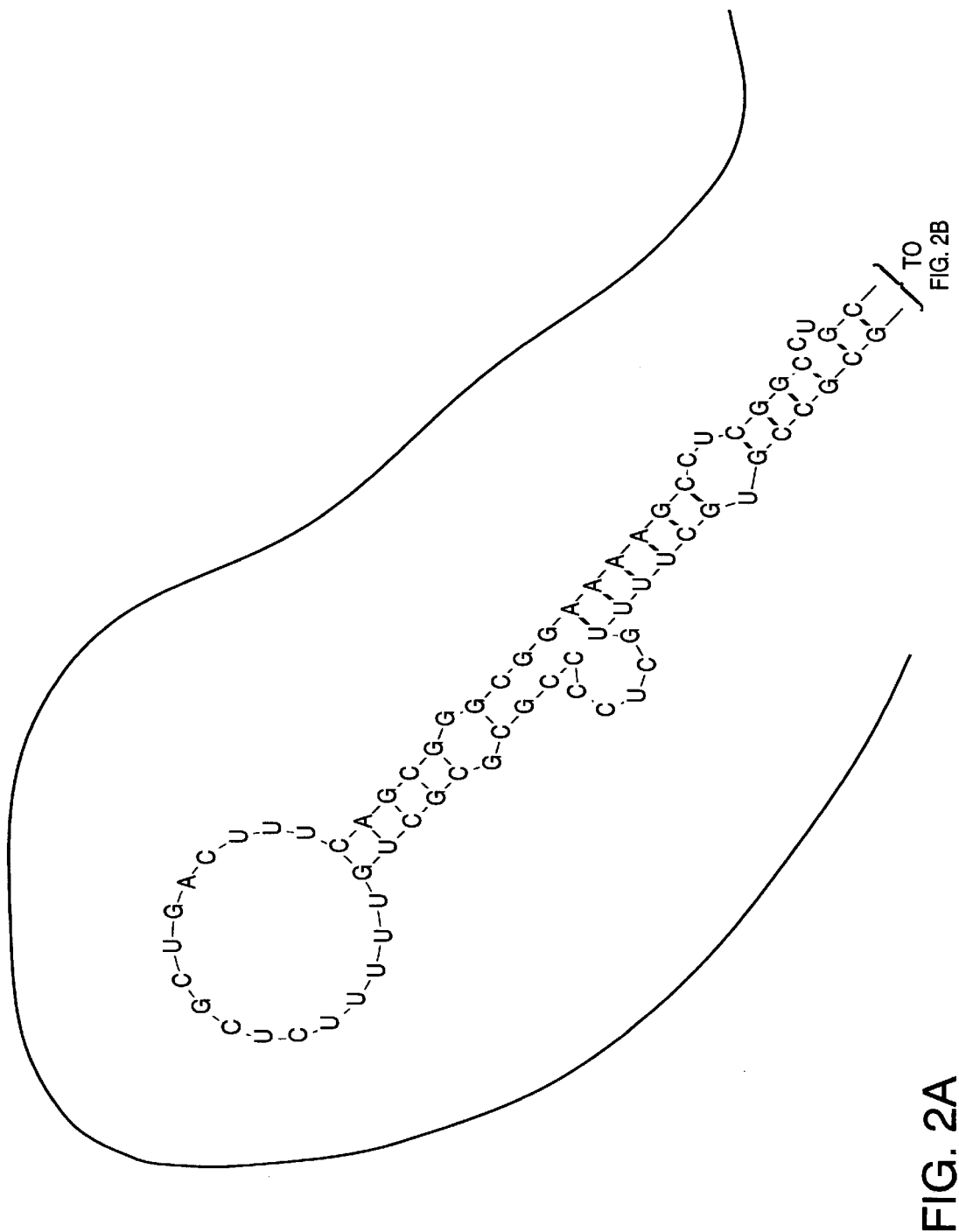
FIGS. 2A and 2B depicts a third region, designated herein as the Y region, of hTR molecule.
Figure 2B:
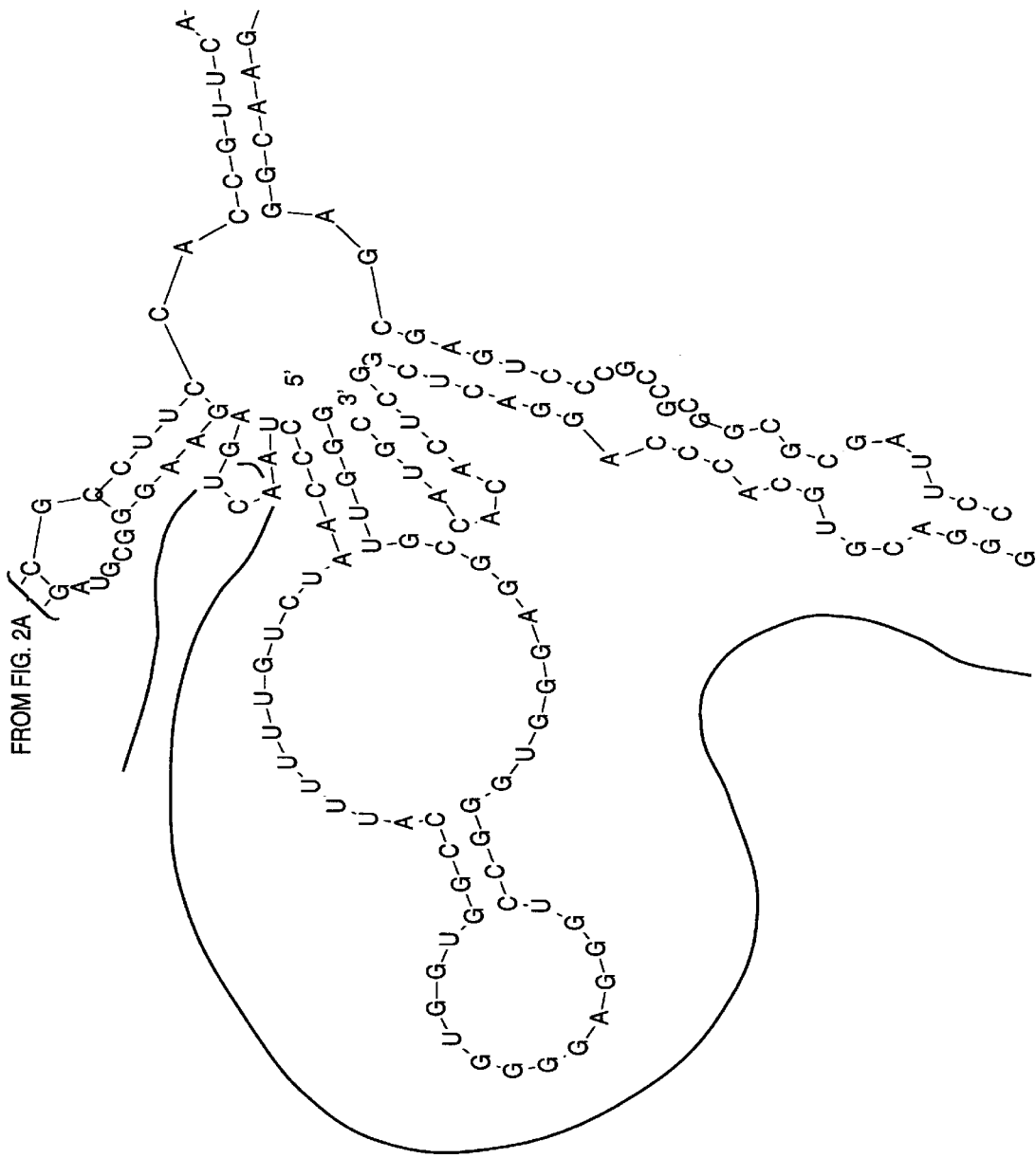

And, a third region, referred herein as the Y region, consists of two domains, referred herein as Y-1 and Y-2. The Y region is depicted in FIGS. 2A and 2B. The Y-1 domain is a short, stem structure of only nine nucleotide pair with a large terminal loop and symmetrical bulge. The Y-2 domain is long double stranded stem with four bulges and a terminal loop. Y-1 and Y-2 domains are connected each to another with single strands segment of hTR, which determine the flexibility of the whole molecule. The Y-1 and Y-2 domains simultaneously anneal to the corresponding epitopes of the first subunit protein component.

The Y region consists of approximately the nucleotides I to and including 148 of SEQ ID No. 1. The Y-1 domain consists of approximately the nucleotides 1 to and including 52 of SEQ ID No. 1. And, the Y-2 domain consists of approximately the nucleotides 59 to and including 148 of SEQ ID No. 1. The Y-1 domain, contains seven nucleotides of the telomer's template sequence, CUAACCC, underlined in sequences above. Seven additional nucleotides spanning the Y-1 and the Y-2 domains, UAAC, complete the telomer's template sequence. Each of these hTR's regions has a unique secondary structure - - - combinations of features (bulges, hairpins, loops) conserved by double stranded stems.

The topological sites of the globular first subunit protein component molecule recognize the unique structure and elements of hTR secondary structure. The first subunit protein and nucleic acid hTR structural elements complement each other, in the manner of nucleic acid aptamers and protein ligands described in processes known as SELEX (Gold et al., 1995). The structural elements are locked in a unique orientation with high specificity and affinity. Thus, the whole telomerase RNA molecule is 'imbedded' into the first subunit protein component in a very specific manner. The stretches of the single stranded nucleotides between and within the regions and the Y-1 and Y-2 domains, on other hand, provide the flexibility for the whole hTR molecule enable the synthesis of telomer's sequences for chromosomal DNA. The features of hTR secondary structure determine the proper orientation and tight binding of each W and X region and Y-1 and Y-2 domains with the first subunit protein component. In the proper orientation, the telomer's template sequence is 'protruding' from the first subunit protein component, remaining accessible for the synthesis of telomeric DNA.

One embodiment of the present invention is a composition. The composition comprises a first RNA molecule and a second RNA molecule. The first RNA molecule has the following formula:

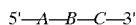

The leter "A" denotes A a section of RNA molecule having 10–100,000 nucleotides, which section is capable of being received by an RNA replicase and with another RNA sequence, F, being replicated. The letter "B" denotes a section of the RNA molecule having approximately 10 to 250 nucleotides in a sequence that has affinity to a subunit protein component of telomerase, which section is capable of binding to such subunit protein component molecule. The letter "C" denotes a section of the RNA molecule having approximately 1 to 10,000 nucleotides which section is capable of being ligated to another RNA sequence, "D".

The second RNA molecule is capable of binding to a target molecule and has the following formula:

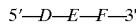

As used above, D is a section of the RNA molecule having approximately 1 to 10,000 nucleotides, which section is capable of being ligated to another RNA sequence, "C". The letter "E" denotes a section of the RNA molecule having approximately 10 to 250 nucleotides in a sequence that has affinity to the subunit protein component of telomerase to which B exhibits affinity, which section is capable of binding to such subunit protein component molecule. The letter "F" denotes a section of the RNA molecule having 10–100,000 nucleotides which section is capable of being received by an RNA replicase and with another sequence, "A", being replicated. The first and the second RNA molecules are capable of forming a third RNA molecule having the following formula:

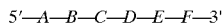

The third RNA molecule is formed by ligation the C and D sections, as the E and the B form secondary structures and are bound to the subunit protein component.

Preferably, the sections B and E each are sections having 10–250 nucleotides and, even more preferred, nucleotides having a sequence of the RNA component of a telomerase molecule or nucleotides having a sequence that has affinity to first subunit protein component or the second subunit protein component of telomerase. A preferred subunit protein component is the first subunit protein component. A preferred telomerase is human telomerase. Preferably, the sections B and E bind to the subunit protein component through non-nucleic acid base pairing interactions. The sections B and E are preferably identified through computer modeling techniques, selected from sequences of the RNA component of telomerase demonstrating an affinity for the first subunit protein component or identified by SELEX techniques. And, most preferred, the B and E sections are selected for a particular functionality, such as binding to certain regions of the first subunit protein component molecule. Preferably, the sequence of the section B is selected from the group of sequences from one region or one domain of a single region of the hTR molecule. The group of regions comprise the W, X, and Y regions. The domains of the group comprise the Y-1 and the Y-2 domains. The sequence of the section E is preferably selected from the same group of regions and domains as B; however, the section E is different from section B.

The nucleotide sequences of the regions and domains selected for sections B and and E of the first and second RNA molecules can be modified. Nucleotides may be added, subtracted and/or substituted. By way of example, without limitation, the sequences defining stems may be moved from one half of the stem to the other. The modifications may be designed by computer modeling techniques or by random mutations to the sequences. Modifications are made which allow each section with such sequence to bind to the target analyte in its specific topological sites, to be ligated by RNA ligase into one functional molecule, and to be a template that could be amplified by Q-beta replicase after its ligation by RNA ligase.

Preferably, the sequences selected for sections B and E have conformational complexity with a high degree of molecular rigidity. Complexity is suggested by sections having secondary structure elements such as symmetrical and asymmetrical bulges, pseudo knots, double stranded hairpins and terminal loops. The elements of the secondary structure are recognized by the first subunit protein component topological sites during the RNA-first subunit complex formation.

Preferably, the elements of the RNA secondary structure exhibit a high degree of stability. That is, the structural elements are present under conditions in which the RNA is combined with the protein component. Such stable structures are kinetically favored and assure consistent folding of recombinant RNA. RNA having stable structural elements will form complexes with the protein component in a consistent efficient manner.

Preferably, the sequences of the regions and domains selected for the sections B and E bind to the first subunit-protein component at two closely situated epitopes. The distance between the epitopes should be capable of being spanned by the sections C and D.

Preferably, modifications, including nucleotide substitutions, deletions and insertions are introduced into the nucleotide sequence of native sequences selected for sections B and E which increase the binding coefficient, promote a particular original secondary structure, or facilitate the manufacture or synthesis of the RNA. By necessity, sections comprising B and E may require the insertion of cloning sites or retain other artifacts of synthesis. These modifications can be evaluated by computer modeling techniques, and empirical evaluation of the modification. Sections B and E, preferably, bind to the first subunit protein component at physiologically normal conditions of pH, temperature, and ionic strength. Buffers for imposing such conditions are known in the art. Buffers, conditions, methods and procedures which are referred herein as being known in the art are described in Sambrook et al., (1989) and other references.

Preferably, the sequences selected for the sections A and F comprise a template for the enzyme Q-beta replicase. RNA sequences which can be serve as a template comprise, by way of example, without limitation, microvariant RNA, nanovariant RNA, midivariant RNA and modifications of such sequences that maintain the ability of the sequences to be replicated by RNA replicase. Preferably, these known sequences are divided to form the the sequences of section A and F. The location of the division is a matter of convenience, influenced by existing cloning sites in the native sequence and the ability to maintain the template characteristics of sequences modified to incorporate cloning sites. Neither section A or F can serve as a template for the enzyme singularly. That is, section A can not be replicated without being ligated to section F, and section F can not be replicated without being ligated to section A. A preferred sequence for section A is set forth in SEQ ID No 2 below:

SEQ ID No. 2
5'-GGGGACCCCC CCGGAAGGGG GGGACGAGGU GCGGGCACCU

CGUACGGGAG UUCGACCGU GACGCUCUAG-3'

A preferred sequence fo section F is set forth in SEQ ID No. 3 below:

SEQ ID No. 3
5'-AGAUCUAGAG CACGGGCUAG CGCUUUCGCG CUCUCCCAGG

UGACGCCUCG UGAAGAGGCG CGACCUUCGU GCGUUUCGGU

GACGCACGAG AACCGCCACG CUGCUUCGCA GCGUGGCUCC

UUCGCGCAGC CCGCUGCGCG AGGUGACCCC CCGAAGGGGG

GUUCCC-3'

In the alternative, a preferred sequence for section A is set forth in SEQ ID No. 4 below:

SEQ ID No. 4
5'-GGGGAAAUCC UGUUACCAGG AUAACGGGGU UUCCUCA-3'

And, a preferred sequence for section F is set forth in SEQ ID No. 5 below:

SEQ ID No. 5
5'-CCUCUCUACU CGAAAGUUAG AGAGGACACAC CCGGAUCUAGC

CGGGUCAACCC A-3'

Figure 3A:
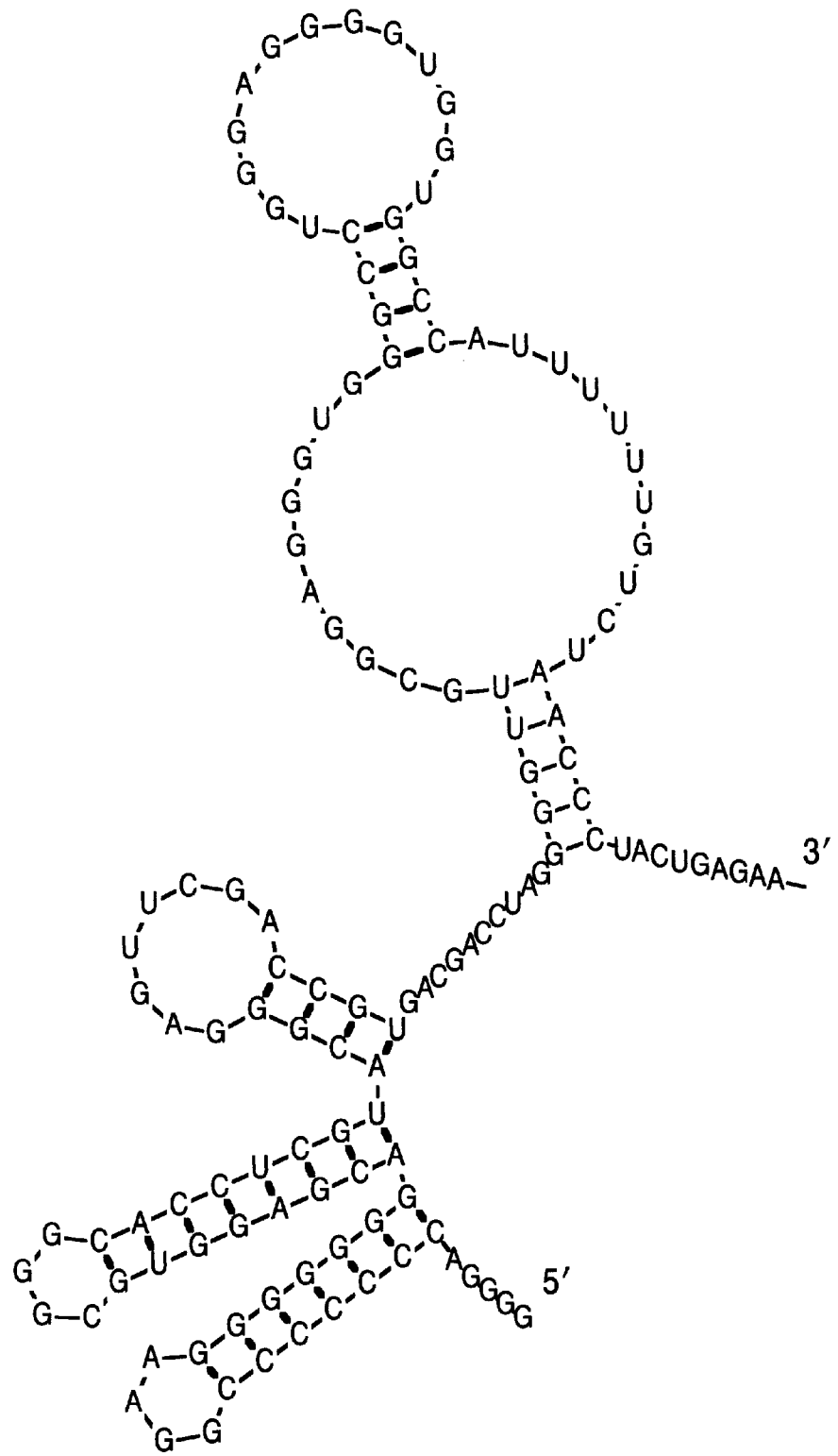
FIGS. 3A, 3B and 3C depict two recombinant RNAs.
Figure 3B:
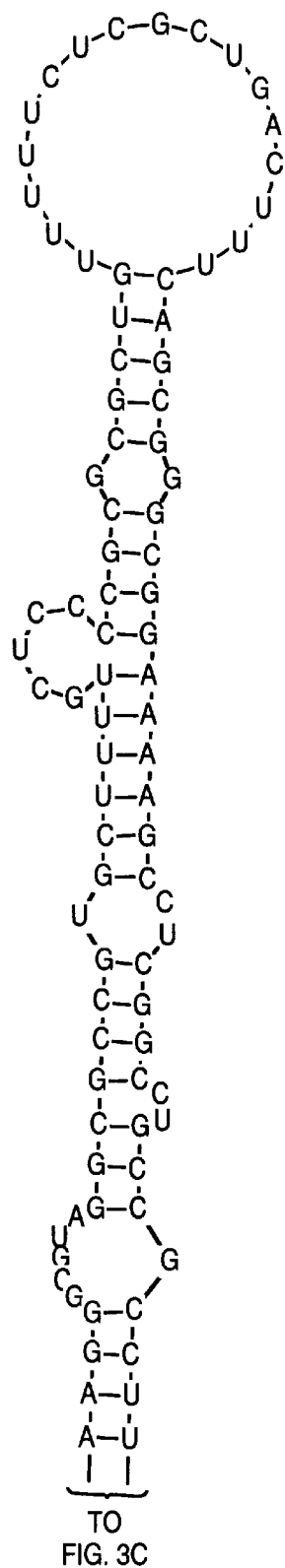
Figure 3C:
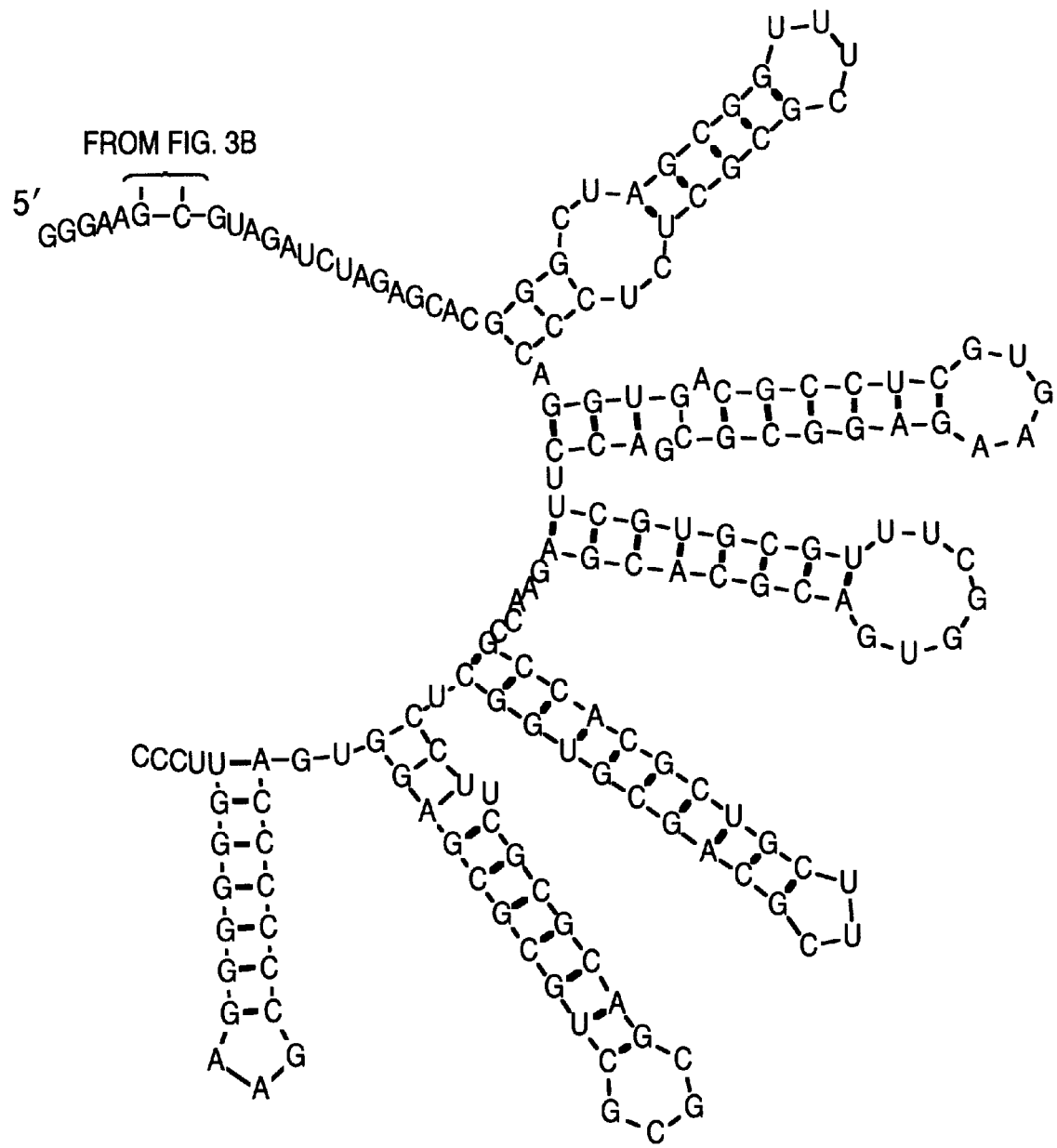

Turning now to FIGS. 3A, 3B and 3C and, in particular, FIG. 3A, FIG. 3A depicts a recombinant RNA with Y-1 domain and Q1 (5'MDV-1 RNA) sequences. This structure conforms to sections A–B of the first RNA molecule. FIGS. 3B and 3C depicts the Y-2 domain and Q2 (3'MDV-1 RNA) sequences. An adjustment, a deletion of a single cytosine nucleotide, show by an arrow, was made to keep the original secondary structures of the Y-1 domain. This structure conforms to the sections E–F of the second RNA molecule.

Turning now to FIGS. 4A and 4B and, in particular, FIG. 4A, FIG. 4A depicts a recombinant RNA with Y-1 domain and QI (5'nanovariant RNA) sequences. This structure conforms to sections A–B of a further embodiment of a first RNA molecule. FIG. 4B depicts a recombinant RNA with Y-2 domain and Q2 (3' of nanovariant RNA) sequences. This structure conforms to the sections E–F of a further embodiment of a second RNA molecule.

Preferably, the sections C and D comprise sufficient nucleotides to span the distance between the sections B and E as such sections B and E are bound to the first subunit component. The sequences selected for the sections C and D are capable of being ligated as the sections B and E are bound to the first subunit component. The sections C and D may comprise random sequences selected for such sequences lack of affinity to the first subunit protein component and inertness to other sequences of the first and second RNA molecules.

Preferably, the sequences of sections C and D are capable of being ligated by RNA ligase. Alternatively, the sequences of sections C and D are capable of recognition by a ribozyme or incorporate ribozyme sequences. The sections C and D may comprise cloning sites required for the synthesis of the first and the second RNAs and cloning sites required to form a divided template sequence for the sections A and F. Bound to the first subunit component and in the presence of ligating conditions, the sections C and D are ligated to form a third RNA which is an active template for a replicase enzyme. Preferably, the section C and D do not align contiguously with each another on the first subunit protein component forming a gap between 20 and 200 angstroms. In forming the third RNA molecule several nucleotides of section C or D may be cleaved. Conditions for ligating RNA with RNA ligase and with ribozymes are known in the art.

Preferably, sections C and D are the nucleotide sequences, termed captomers, in the sense of acceptors and donors. As described, section C naturally terminates in the hydroxyl group required for ligation, and can act as a donor. Section D can serve as an acceptor, with a terminal monophosphate group required by the ligation reaction catalyzed by RNA ligase. A preferred RNA ligase is bacteriophage T4 RNA ligase.

The ligation reactions are performed under standard conditions known to those skilled in the field of molecular biology.

Similar to DNA ligase, T4 RNA ligase catalyzes the formation of a 3'- - - >5' phosphodiester bond between a 3'-terminal hydroxyl and a 5'-terminal phosphate of polyribonucleotide with the hydrolysis of ATP to AMP and Ppi (Silber et al., 1972). The circularization reaction of the oligonucleotides by T4 RNA ligase provides some information on the optimum physical distance between the donor and acceptor parts of a first and second RNA molecule. The optimum is between approximately 1–50 nucleotides, more preferably, 5–25 nucleotides, and, most preferably, a distance of 10–16 nucleotides (Kaufmann et al., 1974, Sugino et al., 1977). The major distinguishing feature of RNA ligase and DNA ligase is that RNA ligase aligns the free ends of the reacting donor and acceptor on its surface, whereas DNA ligase requires a base-paired template that fixes the oligonucleotide ends in close proximity (Engler and Richarson, 1982, Uhlenbeck and Gumport, 1982).

A preferred sequence for section C is set forth as SEQ ID No. 6 and 7 below:

```
    5'-UACUGAGAAA-3'                    SEQ ID No. 6
    and
    5'-UACCGA-3'                        SEQ ID No. 7
```

A preferred sequence for section D is set forth as SEQ ID No. 8 and 9 below:

```
    5'-GGGAA-3'                         SEQ ID No. 8
    and
    5'-GGG-3'                           SEQ ID No. 9
```

A further embodiment of the present invention features a method of determining the presence or absence of a first subunit protein component molecule in a sample. As used herein, the term "sample" means a portion which is representative of the whole. The term includes biopsy material, clinical samples, forensic samples, sputum, saliva, blood and any other material in which the enzyme telomerase may be found.

The method comprises the steps of providing a first RNA molecule and a second RNA molecule. The first RNA molecule is capable of binding to a first subunit protein component molecule and has the formula $$5'-A-B-C-3'$$

The sections A, B and C are as previously described. The second RNA molecule is capable of binding to a first subunit protein component molecule and has the formula: $5'-D-E-F-3'$ The sections D, E and F are as previously described. The method further comprises the step of imposing binding conditions on a sample potentially containing one or more first subunit protein component molecules in the presence of the first and second RNA molecules. In the presence of the first subunit protein component molecule, the first and the second RNA molecules form a ternary complex with such first subunit protein component molecule. The method further comprises the step of imposing RNA ligase reaction conditions on the sample to form a third RNA molecule in the presence of the first subunit protein component molecule. The third RNA molecule has the formula:

$$5'-A-B-C-D-E-F-3'$$

The sample is monitored for the presence of the third RNA molecule, the presence or absence of which is indicative of the presence or absence of a first subunit protein component molecule.

As used herein, "RNA ligase reaction conditions" refers to conditions in which RNA molecules are ligated. Such conditions are known in the art and comprise, by way of example without limitation, the presence of an enzyme, such as RNA ligase, and suitable pH, temperature and the like. Such reactions and conditions are well-known in the art.

Preferably, at least one of the first or second RNA molecules has a signal generating moiety. As used herein, a signal generating moiety refers to a sequence, ligand, enzyme, or chemical entity capable of being detected. By way of example, without limitation, such ligand may comprise an antibody or antigen, biotin or avidin or streptavidin, or a sequence capable or binding to a probe or forming an amplification product. In the presence of the enzyme Q-beta replicase, sequences recognized by the enzyme generate an amplification product. This amplification product can be readily detected with intercalating compounds such as propidium iodide.

After RNA ligase reaction conditions are imposed, the method preferably comprises the further step of separating or enzymatically destroying the RNA molecules unbound with the first subunit protein component molecule and bearing the signal generating moiety. Preferably, the step of degrading the unbound RNA molecules is performed by subjecting the sample potentially containing bound and unbound RNA molecules to enzymatic destruction in the presence of the enzyme reverse transcriptase, and preferably, AML reverse transcriptase. Conditions for the enzymatic destruction of nucleic acids using the enzyme reverse transcriptase are known in the art.

The method, preferably, comprises the further step of hybridization of a primer with a region of the B or E sections with non-paired nucleotides, prior to the template's amplification by Q-beta replicase. The primer has sequences capable of forming a hybridization product with the B or E sections when such sections are unbound to the first subunit protein component. The mixture of first and second molecules, annealed and non-annealed to the subunit, are mixed with the primer and hybridization conditions imposed. The primer binds to the sections of B or E that are unbound to the subunit.

After primer hybridization conditions are imposed, the method preferably comprises the further step of enzymatic degradation of the third RNA molecule resulting from ligation of the first and second RNA molecules which are not bound to the subunit or nonspecifically bound to the target other than telomerase's protein component. Such molecules still bear the signal-generating moiety and, therefore, could be the source of background and false positive results. For this, the mixture is exposed to AML reverse transcriptase. Similarly, the enzyme, with its dual function, will synthesize cDNA complementary to the various regions of non-specifically annealed third RNA and non-ligated first and second RNA molecules and will simultaneously degrade these segments of the RNA template, eliminating those template molecules that are not forming a complex with the subunit protein component.

Preferably, the signal-generating moiety is sections A and F of the third RNA molecule, which sections allow recognition and replication by RNA replicase. Thus, the method further comprises the step of imposing RNA replicase conditions on the sample potentially comprising the third RNA molecule. Preferably, the step of amplifying the bound RNA molecules is performed in the presence of the enzyme Q-beta replicase. Reaction conditions for the enzyme Q-beta replicase are known in the art.

An embodiment of the present invention further comprises a method of making a first RNA molecule and a second RNA molecule, wherein the first RNA molecule has the formula:

$$5'-A-B-C-3'$$

and the second RNA molecule has the formula:

$$5'-D-E-F-3'$$

As used above, the letters A, B, C, D, E, and F are as previously described.

The method comprises the steps of providing a first DNA and a second DNA. The first DNA encodes the first RNA molecule and the second DNA encodes the second RNA molecule. The method further comprises the step of transcribing the first DNA and the second DNA to form the first RNA molecule and the second RNA molecule.

Preferably, the first DNA and the second DNA are provided as sets of complementary oligonucleotides (dsDNA). The sets of first and second DNAs can be multiplied in plasmids when provided with suitable restriction sites and transcription sequences.

Preferably, a first starting dsDNA is made having a formula:

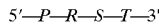
5'—P—R—S—T—3'

And, a second starting dsDNA is made having a formula:

5'—M—N—O—P—3'

As used above, the letter O represents a DNA sequence encoding B or E and the letter "R" represents a DNA sequence encoding B or E which is not O. The letters "M", "P" and "T" represent restriction site linkers. The letters N and S represent nucleotide sequences that encode the section C and D of the first RNA and the second RNA molecules. The first and the second starting dsDNAs are joined with Q-beta template sequences using "M" and "P" restriction sites for the first starting dsDNA, and P and T restriction sites for the second starting dsDNA.

The Q-beta template sequences are placed in a recombinant plasmid as an insert. The organization of the insert in the first recombinant plasmid is:

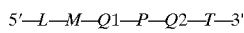
5'—L—M—Q1—P—Q2—T—3'

The letters "M", "P" and "T" represent the restriction sites for cloning the first and second dsDNAs. The letter "L" represents a T7 RNA promoter sequence, the site of the promoter of RNA transcription. The letter "Q I" represents sequences which encode a part of a Q—beta replicase template which corresponds to section A of the first RNA molecule. The letter "Q2" represents sequences which encode a part of a Q—beta replicase template which corresponds to the section F of the second RNA molecule. The plasmid is used to transform competent bacterial cells. The cells are cultured, harvested and the plasmid DNA isolated.

The first recombinant plasmid dsDNA having the insert encoded Q-beta replicase template is subjected to restriction enzyme digestion and recombination with the first and second starting dsDNA to form a second recombinant plasmid and a third recombinant plasmid. The organization of the dsDNA of the second plasmid containing one embodiment of the second dsDNA is set forth below:

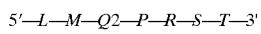
5'—L—M—Q2—P—R—S—T—3'

The second plasmid is used to transform competent bacterial cells. The cells are cultured, harvested and the plasmid DNA isolated. The second plasmid's DNA is transcribed after digestion with T restriction enzyme and using T7 RNA promoter and T7 RNA polymerase to form the first RNA molecule.

The organization of the dsDNA of the third plasmid containing one embodiment of the first dsDNA is set forth below:

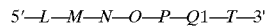
5'—L—M—N—O—P—Q1—T—3'

The third plasmid containing the first starting dsDNA is used to transform competent bacterial cells. The cells are cultured, harvested and the plasmid DNA isolated. The third plasmid's DNA is transcribed after digestion with T restriction enzyme and using T7 RNA promoter and T7 RNA polymerase to form the second RNA molecule.

The organization and composition of the recombinant RNA transcribed from the second recombinant plasmid containing the first starting dsDNA after digestion with T restriction enzyme and using T7 RNA promoter and T7 RNA polymerase is:

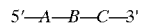
5'—A—B—C—3'

The organization and composition of the recombinant RNA transcribed from the third recombinant plasmid containing the second starting dsDNA after digestion with T restriction enzyme and using T7 RNA promoter and T7 RNA polymerase is:

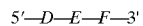
5'—D—E—F—3'

A further embodiment of the present invention comprises a method for construction of the first and the second RNA molecules omitting the cloning of dsDNA in recombinant plasmids. The first and second RNA molecules will be directly transcribed from a machine-synthesized first cDNA encoding the first RNA molecule and a machine synthesized second cDNA encoding the second RNA molecule.

The composition of the first cDNA representing the first recombinant RNA is:

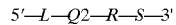
5'—L—Q2—R—S—3'

And, the composition of the second cDNA representing the second recombinant RNA is:

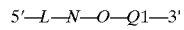
5'—L—N—O—Q1—3'

Wherein the sections represented by the letters L, N, O, Q1, Q2, R, and S are as previously described. These DNAs, with suitable primers, can be amplified with polymerase chain reaction techniques known in the art.

The organization and composition of the first recombinant RNA transcribed from the first synthesized cDNA molecules using T7 RNA promoter and T7 RNA polymerase is:

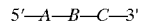
5'—A—B—C—3'

And, the organization and composition of the recombinant RNA transcribed from the second cDNA using T7 RNA promoter and T7 RNA polymerase is:

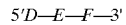
5'D—E—F—3'

The letters A, B, C, D, E, and F are as previously described. These two recombinant RNA transcripts are the first and the second RNA molecules.

A further embodiment of the present invention comprises a kit for determining the presence or absence of a first subunit protein component molecule. The kit comprises one or more reagents comprising a first RNA molecule, a second RNA molecule or DNAs encoding such RNAs. The first RNA molecule has the formula:

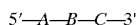

The second RNA molecule has the formula:

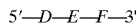

In the presence of a first subunit protein component molecule, the first and the second RNA molecules are capable of forming a subunit-first-and-second-RNA ternary complex and in the presence of RNA ligase means forming a third RNA molecule having the formula:

The letters A, B, C, D, E, and F are as previously described. The third RNA molecule is preferably capable of being received and replicated by RNA replicase.

Figure 5:
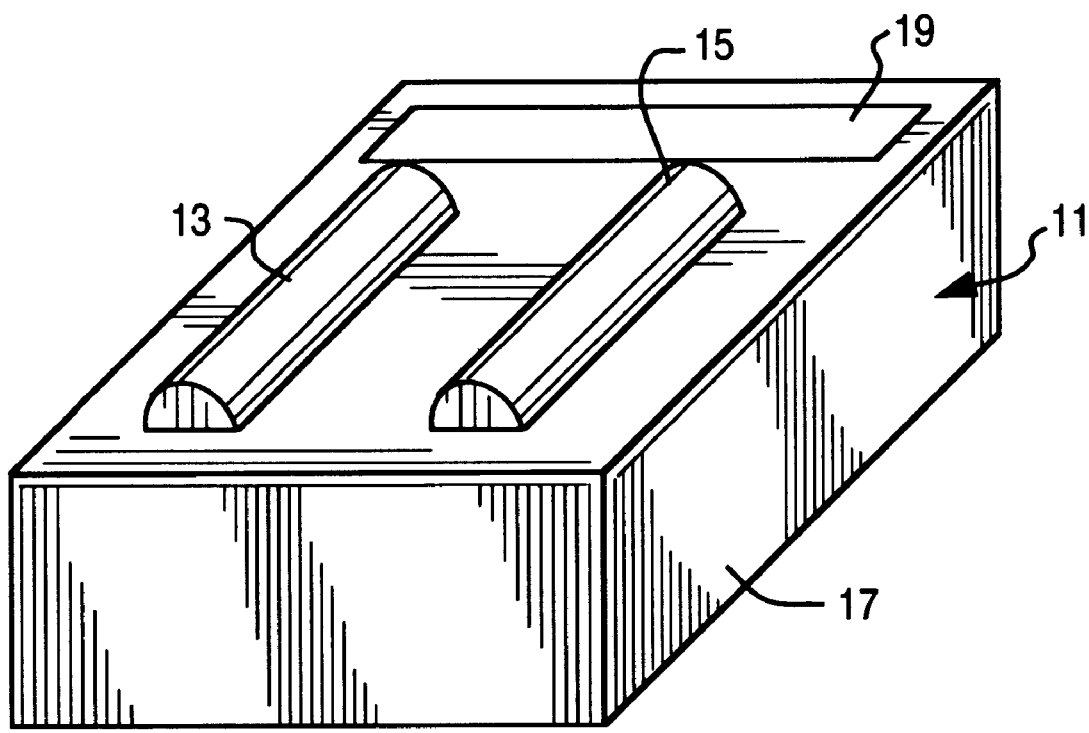
FIG. 5 depicts a kit embodying features of the present invention.

Preferably, the kit further comprises RNA ligase, reverse transcriptase and suitable primers, if necessary. FIG. 5 dipicts a kit, generally designated by the numeral 11, having features of the present invention. Kit 11 has a first vial 13 containing the first RNA molecule and a second vial 15 containing the second RNA molecule. In the alternative, the vials may contain one or more DNAs encoding such RNAs. The kit 11 may also comprise other vials or containment vessels (not shown) containing enzymes, buffers, primers and reagents to facilitate the performance of the methods described herein. Preferably, the kit 11 comprises suitable packaging material, such as box 17, and instructions 19 outlining the methods of the present invention.

Other features will be apparent to those skilled in the art upon reading the following examples.

EXAMPLE 1

Example 1 describes a system in which adenovirus nucleic acid is used as a model for the first subunit protein component of telomerase. Using the above-cited specifics in the RNA ligase action, an experiment was performed in which a first RNA molecule and a second RNA molecule, with sections C and D, captomers, formed a 'loose' ternary complex with a nucleic acid target. This loose ternary complex resembles the complex formed by the first RNA molecule and second RNA molecule with a protein target. The example also highlights the ability of T4 RNA ligase to use such a model complex as a substrate and to restore a template for Q-beta replicase by joining sections C and D of the first and second RNA molecules.

Preparation of the detector probes.

The fifty-base oligonucleotide sequence, SEQ ID No. 10, set forth below, was selected as a model target.

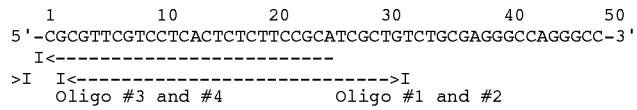

The oligonucleotide sequence contains an Hha I- Pvu II region of the late promoter of adenovirus within map units 16.4 and 16.6 (Ziff and Evans, 1978). It was synthesized on a DNA Synthesizer, together with two pairs of oligonucleotides - - - oligos #1 (SEQ. ID NO. 11) and #2 (Seq. ID No. 12) and oligos #3 and #4 (Seq. ID No. 13) (Seq. ID No. 14).

The first pair of oligos complement each other and represent the counterparts of the adenovirus target region from the nucleotide $C^{25}$ to the 3'-end of the sequence.

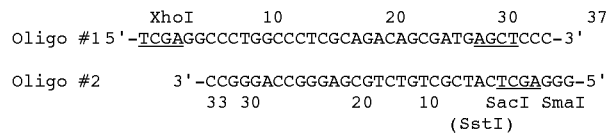

Both oligos have additional sequences representing the complete site for Sac I and a half for Sma I restriction enzymes, and the oligo #1 additionally has a sequence of the Xho I restriction enzyme.

Oligos #3 and #4 represent the other half of the adenovirus target molecule and span from the 5'-beginning of the target sequence to the $T^{21}$ base.

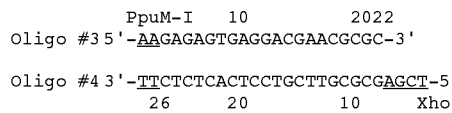

Both oligos #3 and #4 have half of the recognition site for the PpuM-I restriction site and oligo #4 has a sequence of Xho I restriction enzyme, similar to oligo #1. These two pairs of oligos were also annealed and were used for cloning. These two pairs of oligos formed two dsDNA fragments, referred to as the 'PX fragment' and 'XS fragment'. These oligos were used for cloning in the recombinant plasmid pT7 MDV-XhoI.

Figure 6:
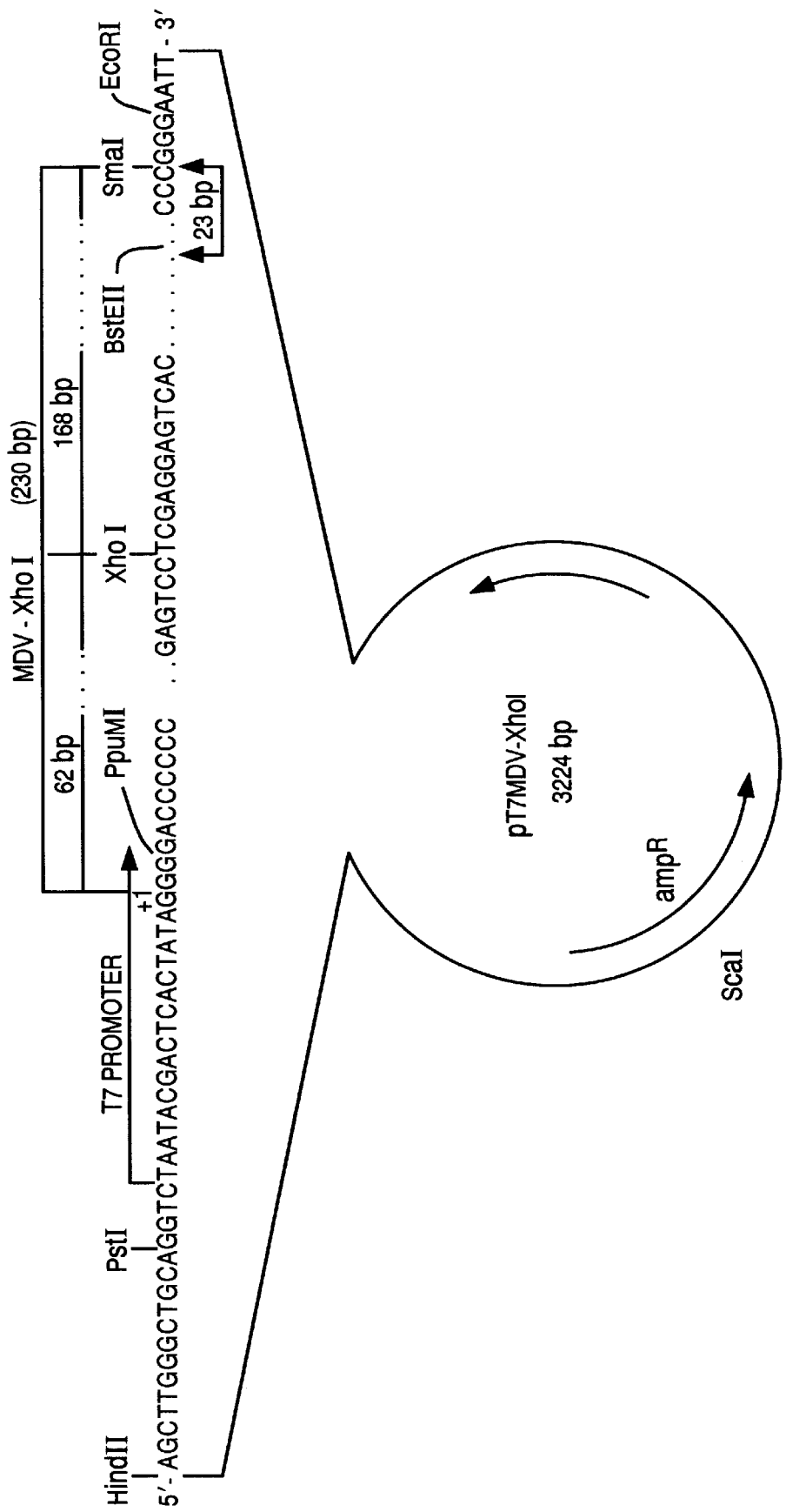
FIG. 6 depicts plasmid pT7 MDV-XhoI.

Turning now to FIG. 6, this figure depicts plasmid pT7 MDV-XhoI. This plasmid was used for cloning of the synthesized PX and XS dsDNAs and for the transcription of the PX and XS recombinant RNA molecules that served as first and second RNA molecules for the adenovirus sequences. This plasmid is a variant of the parent plasmid, pT7 MDV, in which the XhoI linker sequence is not present. For further details of the construction of the vector, see Axelrod et al., 1991.

The pT7MDV-Xho I plasmid DNA was digested either with Ppu MI and Xho I or with Sma I and Xho I restriction enzymes and purified from the excised 65 bp or 166 bp fragments of the cloned MDV cDNA insert. The remaining parts of the pT7MDV-XhoI plasmid after Ppu MI and Xho I digestion (pT7 MDV-1) contained the T7 promoter and 168 bp 3' end of the MDV cDNA. The remaining part of the pT7MDV-Xho I plasmid digested with Xho I and Sma I enzymes (pT7 MDV-2) contained T7 promoter and the 62 bp 5' end of the MDV cDNA. The PX fragment was ligated with the pT7 MDV-1 and the XS fragment was ligated with pT7 MDV-2, forming pPX and pXS recombinant plasmids. The presence of the two different cloning sites in the digested vector ensures only one possible orientation of the inserts in both the pPX and pXS plasmids. Each of these plasmids contains a T7RNA promoter, an insert homologous to part of the target adenovirus sequence, and a segment of the MDV cDNA.

A control recombinant plasmid with target adenovirus DNA insert was constructed as well. For this purpose, we modified the original adenovirus sequence so that it contained Xho I sites at both ends similarly to PX and XS fragments. The fragment was then inserted at the Xho I site of pT7 MDV- Xho I, creating plasmid p325. This plasmid was used either to produce the DNA target sequences or to synthesize the recombinant template MDV RNA with an insert of the adenovirus sequences.

Cold or $^{32}$P-labeled RNA was transcribed from plasmids using 17RNA promoter after the Sma I digestion of pPX or p325 and Sst I or Sma I of pXS digestion according to the standard protocols (Sambrook et al., 1989)

The 193-base RNA transcript from the pPX plasmid is composed of (reading in the 5' - - - >3' direction) the first three G residues of transcription initiation, 22 residues transcribed from the PX fragment and 168 residues transcribed from the 3' end of the MDV cDNA (Seq. ID No. 15):

5'-GGG-AAGAGAGUGAGGACGAACGCGC-3'MDV-1 RNA (168 bases).

The RNA transcript from the pXS plasmid is only 92 bases, shorter than the pT7MDV-1 transcript, and it starts with the 62 residues of the 5' end MDV cDNA and is followed by the 30 residues transcribed from the XS fragment (Seq. ID No. 16):

5'-MDV-1 RNA (62 bases)-GGCCCUGGCCCUCGCAGACAGCGAUGAGCU-3'.

An additional three C nucleotides were generated on 3' end of the XS recombinant RNA after Sma I digestion of the same plasmid.

These two recombinant RNAs represent a set of the first and second, PX and XS, detector RNA molecules. Each of these molecules has three functional parts: amplification, recognition and ligation.

Annealing experiments

PX detector was $^{32}$P end-labeled to monitor the results of the annealing experiments. For this we used bacterial alkline phosphatase (BAP) and bacteriophage T4 polynucleotide linase. Both reactions, dephosphorylation and end-labeling, were performed according to standard protocols (Sambrook et al., 1989). Incorporation of the radioactive label was measured in aliquots of the reaction and the percentages of incorporation were calculated.

The annealing reaction products between the PX and XS detector-molecules and adenovirus target sequences were characterized. The annealing reaction was performed with PX and XS RNAs but without adenovirus target molecules. Three separate annealing reactions with PX, XS and adenovirus target molecules were performed. PX recombinant RNA was $^{32}$P end-labeled using standard methods. Annealing was achieved by boiling the reaction mix two minutes and then incubating it at 65° C. for two hours. The annealing reaction was carried out in a solution containing 50 mM TRIS pH 7.8, 5 mM MgCl$_2$, 0.5 mM ATP and 1 mM EDTA, 10% non-denaturing PAGE at 500 volts for eight hours.

Several bands in a range from 300 nt to 190 nt were seen on autoradiographs. The most plausible explanation of the results is that the 300 nt band results from the annealing of the target DNA molecule with both RNAs. Such complex is composed of from 50 bp double stranded heteroduplex of target/probes segment and 168 bases 3'-end and 62 bases 5'-end of MDV-I. The lowest band is 193 nucleotides of non-hybridized PX RNA and one of the middle bands, with a size of 243 bases, is a complex between PX RNA and adenovirus DNA molecules. The origin of the second band of similar size is unknown.

The efficiency of hybridization was calculated as a percentage of the radioactivity of the top band from the total radioactivity applied on the gel. Usually more than 50% of the total number of PX RNA molecules participate in hybridization with the adenovirus target molecule by itself or in compound with XS. The yield of the ternary complex formed by two RNA detector molecules and the target molecules was, usually, close to 30–40%.

The diagram below illustrates a possible hybridization configuration between the target adenovirus sequence (Seq. ID No. 17) and the two RNA transcripts (Seq. ID No. 18). The SX RNA detector, in this case, was generated by Sst I digestion of the pSX plasmid.

```
1          10         20   24       30            40           50
CGCGTTCGTCCTCACTCTCTTCC-G-CATCGCTGTCTGCGAGGGCCAGGGCC
GCGCAAGCAGGAGUGAGAGAAGG   GUAGCGACAGACGCUCCCGGUCCCGG
|PX detector molecule G    A   XS detector molecule |
\                            U-C-G
168 bases of MDV-1 RNA-3'  5'-62 bases of MDV-1 RNA
```

There is complete complementarity along the PX RNA detector and the first 23 bases of the target molecule, but not the last, the 24th G-residue of the transcript and the G-base of the adenovirus target molecule. The first four bases of the XS detector (UCGA) do not have homologous nucleotides on the target DNA molecule, although the rest of the transcript is complementary to the target molecule. Thus, the hybridized RNA transcripts do not juxtapose to the target, in end-to-end fashion, but rather leave a ~20 Angstrom gap between the terminal hybridized nucleotides.

The G and UCGA nucleotides of the PX and XS detector probes are the the sections C and D, captomers, of the first and second RNA molecules. They do not hybridize to the target and comprise structures similar to the donor/acceptor complex, which is necessary in order for RNA ligase to form a phosphodiester bond (Uhlenbeck, 1983). The G captomer is a donor with a 5'-phosphate terminus and the UCGA captomer is an acceptor with a 3'-hydroxyl terminal group on the U residue.

Ligation experiments

The recombinant plasmid pXS was constructed in a such way that it could be linearized either with SmaI or SstI for RNA transcription (See Diagram above). The two XS RNA detector molecules are different in the total lengths and composition of their captomers. The XS detector generated with Sst I digestion had a captomer of four UCGA-base-long bases, whereas the captomer generated after the Sma I digestion was longer for the three Cs.

Ligation reactions were carried out on 4 µl aliquots taken directly from the annealing reactions in the presence of the 10nM mercaptoethanol, and 40 Units of T4 RNA ligase at 25° C. after confirmation by gel electrophoresis that hybridization was successful. The duration of the reaction varied from 2 hours to overnight. The bands representing ligation products composed of PX-SX ligated detector molecules were excited and their radioactivity was measured and compared with the total radioactivity of the aliquot from the annealing reaction used for the ligation.

Several bands, with a maximal band of approximately 300 nt were seen on the autoradiographs of the electrophoresed products after the ligation reaction. Products of the ligation reaction and non-ligated PX transcripts were seen on the autoradiographs. The products of the annealing reactions, which were performed with PX and XS transcripts without the target adenovirus DNAs, served as a negative control. Only PX transcripts were seen compared with Control p325 RNA transcripts. The total volume of each ligation reaction was 10 µl, with the final concentrations 10 mM, 5 mM MgCl$_2$ and 2 Units of T4 RNA ligase in the presence of 20% PEG. The reaction was performed at 25° C. and ended by adding 1 µl of 100 mM EDTA, 7M Urea denatured 10% PAGE at 500 volts for eight hours of electrophoresis.

Additionally, the duration of the reaction apparently does not affect the rate of ligation when the long captomers were used. The yield of the ligated product was 20.0% after two hours of reaction and 18.7% after overnight. The longer reaction time, however, might have a certain disadvantage when the short captomers are used. The overnight reaction yielded 18.4% compared with 33.2% after two hours of reaction. The reduction in the percentages of ligated products after a prolonged reaction time apparently indicates that the ligation products composed of PX and XS RNA transcripts are not stable and dissociate over time. The results of the ligation experiment demonstrates that the length of the XS captomer seemingly does not effect the ligation rate of the RNA transcripts, although the highest ligation rate was observed when the acceptor-captomer was composed of the seven-AGCUCCC-residues. $^{32}$P-labeled recombinant MDV-I RNA, with the adenovirus insert transcribed from the p325 plasmid, served as a reference marker.

TABLE 1

Effect of the captomer's length on the yield of the ligation products between PX and XS RNA transcripts. 4 ul aliquots of the annealing reactions (1–6*) with two RNA transcripts and adenovirus target DNA were used for the subsequent ligation reaction. 4 ul aliquots of the annealing reaction (7**) without the target DNA were used as the negative control.

| Test # | Length of captomer used in the reaction | Duration of reaction at 25° C. | Total counts (cpm) of the band in the gel | Their proportion (%) from the counts loaded |
|---|---|---|---|---|
| 1. | Short[1] | 2 hours | 3428 | 20.0% |
| 2. | Short | o/n | 3140 | 18.7% |
| 3. | Long[2] | 2 hours | 5576 | 33.2% |
| 4. | Long | 2 hours | 1657 | 9.9% |
| 5. | Long | o/n | 3085 | 18.4% |
| 6. | Long | o/n | 1385 | 8.2% |
| 7. | Long | 2 hours | 98 | 0.01% |

*16.800 cpm were loaded into each test lane
**76.700 cpm were loaded into a control lane The short (UCGA) captomer was generated by the pXS plasmid DNA digestion by the Sst I restriction enzyme, and the long (AGCUCCC) captomer resulted from the digestion of the pXS plasmid DNA by the Sma I restriction enzyme.

The ligation product composed of the ligated PX and XS RNA detector molecules was purified by gel electrophoresis. The purified product was used as a template for Q-beta replicase.

Amplification of the ligation products by Q-beta replicase

Q-beta replicase reactions were carried out on a volume of 20 µl at 37° C. during 25–30 minutes in 50 -µl reactions containing 88 mM Tris-HCL (pH 7.5), 12 mM MgCl$_2$, 0.2 mM of each ribonucleoside triphosphate, 25 uCi of [alpha-$^{32}$P]GTP, 90 pm/ml of Q-beta replicase, and 11.2 pm/ml of template RNA. From this mixture, 7 to 15 µl was applied directly onto a denaturing polyacrylamide gel containing 7M Urea for electrophoretic analysis. Additionally, adsorbed radioactivity was determined by liquid scintillation.

The Q-beta replicase experiment demonstrates that there are no templates for Q-beta enzyme in the aliquots representing the tube in which the ligation was performed without the adenovirus target, which indicate that target analyte was necessary to unite two detector probes. A ligation reaction was performed on aliquots of the annealing reaction. The 5 µl aliquots from each reaction were analyzed on a non-denaturing gel. An aliquot from the annealing reaction without the adenovirus target sequences, with adenovirus sequence and without PEG, and in the presence of the target adenovirus sequences and PEG were compared to the Q-beta replicase products of pT7 MDV-XhoI plasmid as a control. The data indicated that amplification of the template by Q-beta replicase occurred only when ligation of the PX and XS RNA detector molecules took place in the presence of the target.

EXAMPLE 2.

This Example features a Q-beta replicase-based system of paired detector-molecules which can be constructed and used to identify a first subunit protein component target. This example will feature detector molecules with sections B and E having sequences of the Y-1 or Y-2 domains of hTR. These domains are situated near each another in hTR. The single stranded sequences with a section of the telomere's sequence spanning the two domains are used as the sections C and D, captomers. These captomer sequences comprise a donor and an acceptor accessible for T4 RNA ligase (FIGS. 2A and 2B).

A computer analysis of the secondary structures of the detector molecules with MDV-1 RNA template as a reporting system and Y-1 and Y-2 as a detector system showed that the secondary structure of Y-1 and Y-2 domains remain intact. Thus Y-1 and Y-2 sequences will be recognizable by the corresponding topological sites of the first subunit protein component after being incorporated into the recombinant RNA. A small modification (minideletions) will be introduced into the nucleotide sequence of the first detector molecule to protect the original secondary structure of the Y-1 segment without compromising the ability of the whole molecule to be ligated by RNA ligase and to be amplified by Q-beta replicase (FIGS. 3A).

To construct first and second RNA molecules, two dsDNA will be synthesized. The first dsDNA will represent 58nt of the Y-1 domain with terminal Xho1 and Eco RI sites (Seq. ID No. 19 and Seq. ID No. 20), and another dsDNA, will represent 91 nt of the Y-2 domain with terminal PpuI and XhoI sites (Seq. ID No. 21 and Seq. ID No. 22). Such two dsDNAs will be cloned in a pT7 MDV-Xho I plasmid (FIG. 6), using the same strategy and procedures as was described in the above experiments with adenovirus sequences.

No. 23) a telomere's template sequences that should be modified by a single (A) nucleotide deletion to preserve a secondary structure of the Y-1 domain. The template sequences will be followed by the terminal 3 nt (UGA) of Y-1 hTR and Eco RI (GAA) sequence, which represented the donor captomer, naturally terminated with the hydroxyl group required for ligation. The second recombinant RNA is started with the transcriptional (GGG) and PpuMI (AA) nucleotides. These five nucleotides composed an acceptor captomer. It should follow by the sequences of C-2 domain and MDV-I RNA regions. The secondary structures of the two recombinant RNA are shown in FIGS. 3A, 3B and 3C.

Normally after synthesis, the 5' end of the second recombinant molecule would contain a triphosphate group, which cannot participate in ligation. However, in addition of providing quanosine triphosphate as a precursor for transcription of the second recombinant RNA, a 20-fold excess of guanosine monophosphate should be provided. The monophosphate will be incorporated into the 5' termini, assuring that most second recombinant molecules will contain the monophosphate group required for ligation (Tyagi et al., 1996). Such procedures for substitution of triphosphate in the 5' termini should be omitted during a construction of the first recombinant RNA. This molecule will have triphosphate at the 5' termini, which prevents a ligation of 5' and 3' ends of MDV template.

EXAMPLE 3

A computer analysis of the secondary structures of the detector molecules with nanovariant RNA template as a reporting system (Schaffner et al., 1977) and Y-1 and Y-2 as

```
    XhoI
5'-TCGA-GGGGTTGCGGAGGGTGGGCCTGGGAGGGGTGGTGGCCATTTTT
       3'-CCCCAACGCCTCCCACCCGGACCCTCCCCACCACCGGTAAAAA
TGTCTAACCCTACTGA-GAA-3'
ACAGATTGGGATGACT-CTT-5'
                EcoRI

PpuMI
5'-AA-GAAGGGCGTAGGCGCCGTGCTTTTGCTCCCCGCGCGCTGTTTTT
3'-TT-CTTCCCGCATCCGCGGCACGAAAACGAGGGGCGCGCGACAAAAA
CTCGCTGACTTTCAGCGGGCGGAAAAGCCTCGGCCTGCCGCCTTCGT-3'
GAGCGACTGAAAGTCGCCCGCCTTTTCGGAGCCGGACGGCGGAAGCA-AGCT-5
                                                 XhoI
```

The recombinant plasmids for a synthesis of two recombinant RNA transcripts, composed of the hTR and Q-beta replicase template sequences, will be used similarly to those of the PX and XS for adenovirus, employing T7 RNA promoter and T7RNA polymerase.

The first 62 nt at the 5' end of the first recombinant RNA are 5'-terminal sequences of MDV-1 RNA followed by Y-1 domain sequences with 10 nt (CUAACCCUAC) (Seq. ID a detector system showed that the secondary structure of Y-1 and Y-2 domains remain intact, similarly to the detector molecules with MDV-1 RNA template.

For this, 114 bases oligonucleotide (Seq. ID No. 24) composed of T7 RNA promoter sequences followed by the 34 nucleotides of the 5 end nanovariant RNA and Y-1 hTR domain sequences will be synthesized.

```
        T7 RNA promoter      5' end nanovariant RNA
5'-ATTATGCTGAGTGATATCCC-
CTTTAGGACAATGGTCCTATTGCCCCAAAGGAGA- Y-1 hTR domain
CCCAACGCCTCCCACCCGGACCCTCCCCACCACCGGTAAAAAACAGATTGGGATGAC
T-3'
```

Another oligonucleotide (SEQ ID NO. 25) of 165 bases started with T7 RNA promoter followed by 3rd hTR domain and 54 nucleotides of 3' end nanovariant RNA sequences will be composed.

```
        T7 RNA promoter              Y-2 hTR domain
5'-ATTATGCTGAGTGATATCCC-TTCCCGCATCCGCGGCACGAAAACGAGGGGCGCGC
GACAAAAAGAGCGACTGAAAGTCGCCCGCCTTTTCGGAGCCGGCGCCTTTTCGGAG
CCGG- 3' end nanovariant RNA
CCAGAGATGACGTTTCAATCTCTCCTGTGTGGGCCTAGATCGGCCCAGTTGGGT-3'
```

Figure 4A:
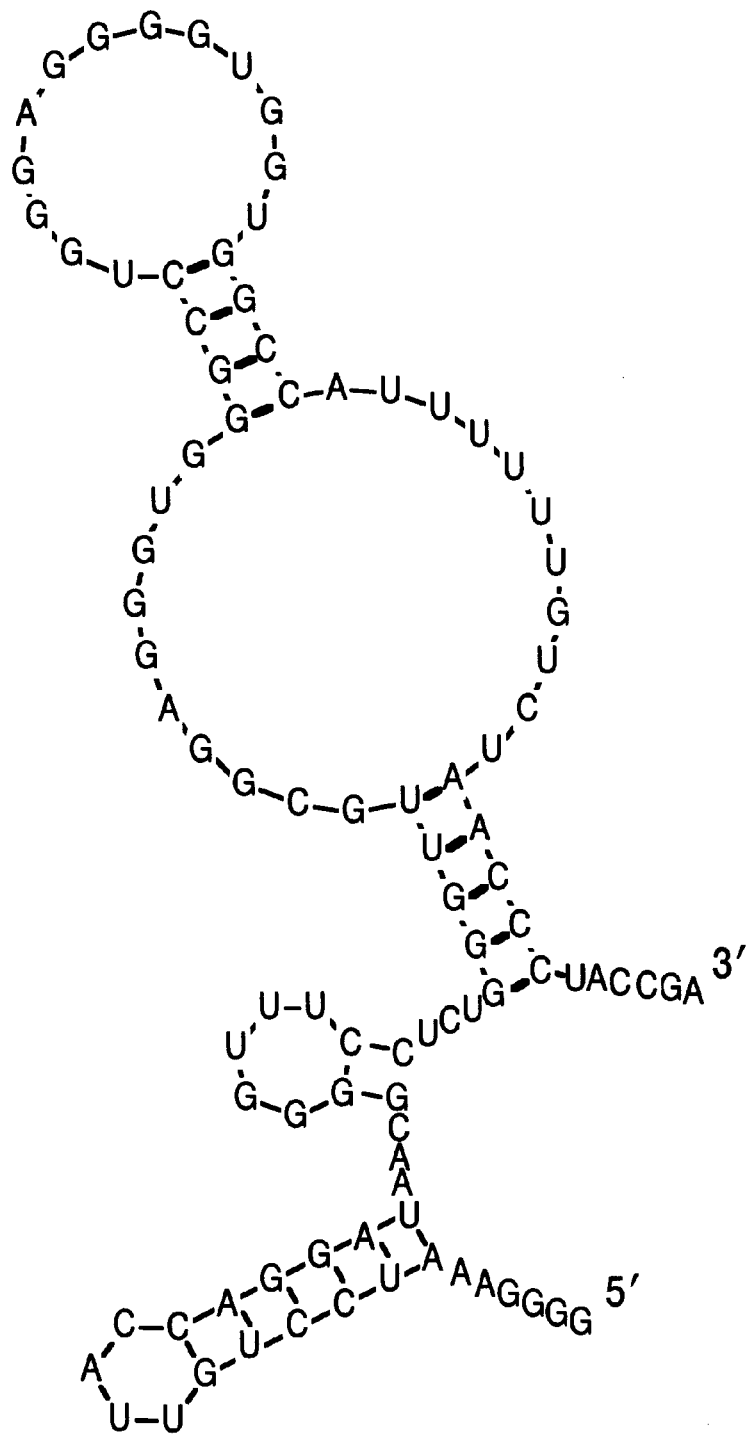
FIGS. 4A and 4B depict two recombinant RNAs.
Figure 4B:
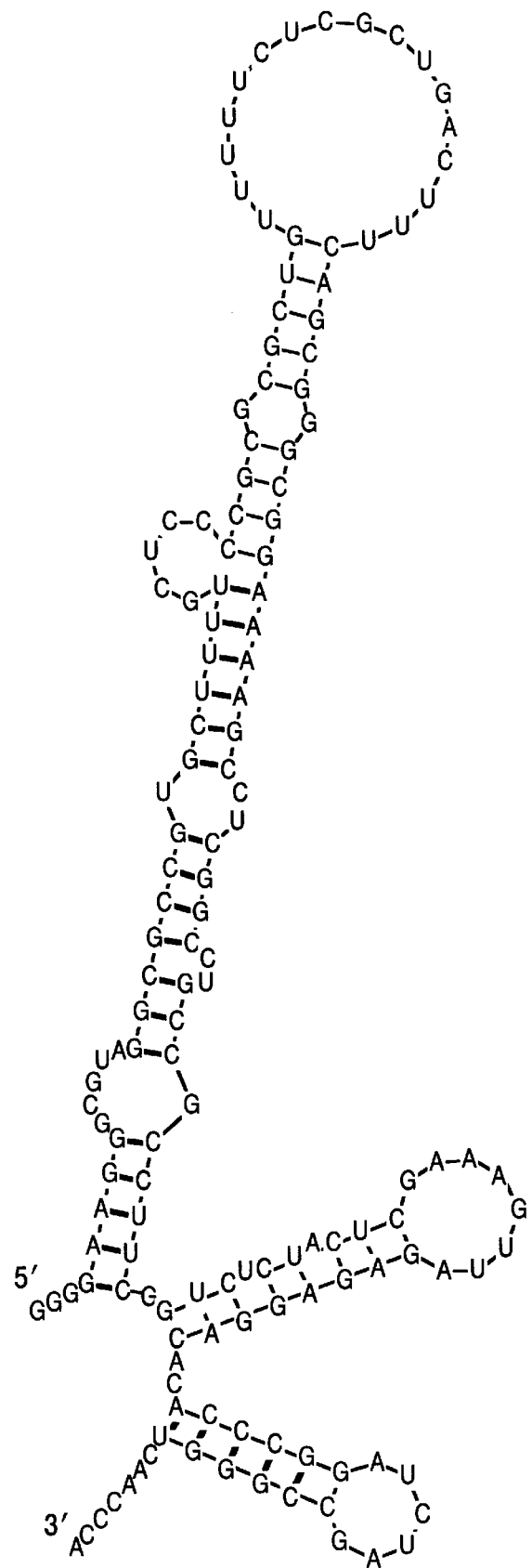

The synthesis of cDNA templates will allow to omit the laborious construction of the recombinant plasmid with cDNA representing the nanovariant sequences and cloning of ds DNA representing Y-1 and Y-2 hTR in such plasmid. These two oligonucleotides will be used directly as templates to synthesize two recombinant detector RNA molecules composed hTR and nanovariant RNA sequences, using the standard procedures of in vitro RNA synthesis (Sambrook et al., 1989). These procedures are known in the art The complete secondary structure of these two RNA molecules are shown in FIGS. 4A and 4B. The compositions of the recombinant RNA molecules with nanovariant RNA sequences is similar to those of with MDV-I RNA, except that the donor captomer is composed of 6nt (UACCGA) and the acceptor captomer is composed of 3nt (GGG).

The secondary structure of Y-1 and Y-2 domains sequences in the four recombinant RNAs have the same secondary structure as these domains in the native hTR. The single stranded spacers between hTR domain and Q-beta replicase sequences will provide enough flexibility for the Y-1 and Y-2 domains of the recombinant RNA molecules to bind to the first subunit protein component in the corresponding epitopes as Y-1 and Y-2 domains of the native hTR. Neither of the two recombinant RNA molecules can serve as a template for Q-beta replicase. However, the two recombinant RNA molecules of the particular set will form a functional template after binding with to the subunit and ligation by T4RNA ligase.

Thus, while preferred embodiments have been illustrated and describe, it is understood that the present invention is capable of variation and modification and, therefore, should not be limited to the precise details set forth, but should include such changes and alterations that fall within the purview of the following claims.

REFERENCES

U.S. PATENT DOCUMENTS

Martinelli RA., Donahue JJ. and Unger T. 1995. Amplification of Midivariant DNA Templates. U.S. Pat. No. 5,407, 798

Villenponteau B., Feng J., Funk W., and Andrews W. H. Mammalian Telomerase. U.S. Pat. No. 5,583,016

OTHER PUBLICATIONS

Axelrod VA., Brown E., Priano C. and Mills DR. 1991. Virology, 184, 595–608

Collins K., Kobayashi R. and Greider CW., 1995. Cell 81, 677–688

Dreyfuss G., Matunis M.J., Pinol-Roma S. and Burd C.G. 1993. Annu. Rev. Biochem. 62, 289–321

Engler MJ. and Richardson CC. 1982. The enzymes. Academic Press, Inc. vol XV. 3–29.

Feng J. Funk WD, Wang S-S., Weinrich SL., Avillion AA., Chiu C-P., Adams RR., Chang R., Allsopp RC., Yu J., Le S., West MD., Harley CG., Andrews WH., Greider CW. and Villeponteau B. 1995. Science 269, 1236–1241.

Gold L., Polisky B., Uhlenbeck O, and Yarus M. 1995. Ann. Rev. Biochem. 64, 763–797.

Kaufmann G., Klein T. and Littauer UZ. 1974. FEBS Lett. 46, 271–275.

Kim NW., Piatyszek MA., Prowse KR., Harley CB., West MD., Ho PLC., Coveille GM., Wright WE., Weinrich SL., and Shay JW. 1994. Science. 266, 2011–2015

Nelson NJ. 1996. J. Natl. Cancer Inst. 88,1021–1023

Ohyashiki JH., Ohyashiki K., Sano T. and Toyama K. 1996. Jpn. J Cancer Res. 87, 329–331

Sambrook J., Fritsch EF and T. Maniatis. 1989. Molecular Cloning. Cold Spring Harbor Laboratory Press.

Schaffner W., Ruegg KJ. and Weissmann C. 1977. J Mol. BioL 117, 877–907.

Silber R. Malathi VG. and Hurwitz J. 1972. Proc. Natl. Acad. Sci. USA 69, 3009–3013

Sugino A., Goodman HM., Heyneker HL., Shine J., Boyer HM. and Cozzarelli NR. 1977. J. Biol.Chem. 252, 3987–3987

Tyagi S., Landergen U., Tazi M., Lizardi PM. and Kramer FR. 1996. Proc. Natl. Acad. Sci. USA. 93, 5395–5400.

Uhlenbeck OC and Gumport RD. 1982. The enzymes. Academic Press, Inc. vol XV. 31–58.

Uhlenbeck OC. 1983. TIBS. March, 94–96.

Wright WE., Shay JW. and Piatyszek MA. 1995. Nucleic Acid Res. 23, 3794–3795

Zaug Aj., Lingner J. and Cech T. 1996. Nucleic AcidRes. 24, 523–533

Ziff EB. and Evans RM. 1978. Cell 15, 1463–1475.

What is claimed is:

1. A first ribonucleic acid (RNA) molecule and a second RNA molecule for use in determining the presence or absence of a first subunit protein component of a telomerase molecule, said first RNA molecule binding said first subunit protein component under binding conditions and having the following formula:

$$5'-A-B-C-3'$$

wherein A is a section of the RNA molecule having 10–100,000 nucleotides which section is, with another RNA sequence, F, replicated by an RNA replicase, the letter "B" denotes a section of the RNA molecule having approximately 10 to 250 nucleotides comprising sequences from the Y region of human telomerase which section specifically binds to said first subunit protein component of under binding conditions, and the letter "C" denotes a section of the RNA molecule having approximately 1 to 10,000 nucleotides which section is ligated to another RNA sequence, "D"; under ligation conditions, said second RNA molecule binding said first subunit protein molecule under binding conditions and having the following formula:

$$5'-D-E-F-3'$$

wherein D is a section of the RNA molecule having approximately 1 to 10,000 nucleotides which section is ligated with another RNA sequence, "C", under ligation conditions, the letter "E" denotes a section of the RNA molecule having approximately 10 to 250 nucleotides comprising sequences from the Y region of human telomerase which section specifically binds said first subunit protein component under binding conditions, and the letter "F" denotes a section of the RNA molecule having 10 to 100,000 nucleotides which section is, with another sequence, "A", replicated by said RNA replicase; said the first and the second RNA molecules forming a third RNA molecule upon ligation of sections C and D, which third RNA molecule has the following formula:

$$5'-A-B-C-D-E-F-3'$$

said third RNA molecule formed by ligating the C and D sections, as the E and the B sections are bound to said first subunit protein component, said third RNA for being replicated by said RNA replicase as an indication of the presence or absence of the first subunit protein component.

2. The RNA molecules of claim 1 wherein said sections denoted by the letters "A" and "F" represent sequences selected from the group of sequences consisting of MDV-I RNA, Q-beta RNA microvariant RNA, nanovariant RNA, midivariant RNA and modifications thereof which maintain the ability of the sequences to be replicated by Q-beta replicase.

3. The RNA molecules of claim 1 wherein the sections B and E bind to said first subunit protein component through non-nucleic acid pairing interactions.

4. The RNA molecules of claim 1 wherein said first subunit protein component is derived from humans.

5. The RNA molecules of claim 1 wherein the B and E sections have at least one sequence of the RNA component of a human telomerase enzyme.

6. The RNA molecules of claim 1 wherein the sections C and D together define a site for ligation.

7. A method of determining the presence or absence of a first subunit protein component of the enzyme telomerase, said method comprising the following steps:

a) providing a first RNA molecule and a second RNA molecule, said first RNA molecule binding said first subunit protein component under binding conditions and having the following formula:

$$5'-A-B-C-3'$$

wherein A is a section of said RNA molecule having 10 to 100,000 nucleotides which section is, with another RNA sequence, F, replicated by an RNA replicase and the letter "B" denotes a section of the RNA molecule having approximately 10 to 250 nucleotides comprising sequences from the Y region of human telomerase which section specifically binds said first subunit protein component under binding conditions, and the letter "C" denotes a section of the RNA molecule having approximately 1 to 10,000 nucleotides which section is ligated to another RNA sequence, "D"; under ligating conditions, said second RNA molecule binding to said first subunit protein component under binding conditions and having the following formula:

$$5'-D-E-F-3'$$

wherein D is a section of the RNA molecule having approximately 1 to 10,000 nucleotides which is ligated to another RNA sequence, "C", under ligating conditions and the letter "E" denotes a section of the RNA molecule having approximately 10 to 250 nucleotides comprising sequences from the Y region of human telomerase which section specifically binds said first subunit protein component under binding conditions, and the letter "F" denotes a section of the RNA molecule which section is, with another sequence, "A", replicated by an RNA replicase; said first and the second RNA molecules forming a third RNA molecule, upon ligation of the sections C and D, having the following formula:

$$5'-A-B-C-D-E-F-3'$$

said third RNA molecule formed by ligating the C and D sections, as the E and the B sections are bound to said first subunit protein component, said third RNA molecule for being replicated by said RNA replicase as an indication of the presence or absence of said first subunit protein component;

b) combining a first sample potentially containing said first subunit protein component with said first and said second RNA molecules and imposing conditions which allow said first and said second RNA molecules and said first subunit protein component to form a first second RNA molecule subunit complex, to form a second sample;

c) imposing RNA ligase conditions on said second sample to form said third RNA molecule in the presence of said first subunit protein components to form a third sample;

d) imposing amplification conditions on said third sample to form an amplification product in the presence of said first subunit protein component, to form a fourth sample; and e) monitoring said fourth sample for the presence or absence of the third RNA molecule as indicative of the presence or absence of said first subunit protein component.

8. The method of claim 7 further comprising the step of removing first and second RNA molecules which do not form a complex after forming said second sample.

9. The method of claim 8 wherein said first and second RNA molecules which do not form a complex are enzymatically destroyed.

10. The method of claim 9 wherein said first and second RNA molecules are destroyed by combining at least one of said second, third or fourth samples and said first and second RNA molecule with the enzyme reverse transcriptase and imposing reverse transcriptase reaction conditions on a said sample.

11. The method of claim 7 wherein said amplification conditions comprise combining said third sample potentially containing said third RNA molecule with the enzyme Q-beta replicase.

12. The method of claim 7 wherein said sections denoted by the letters "B" and "E" have one or more sequences of the RNA component of human telomerase.

13. The method of claim 7 wherein the sections denoted by the letters "A" and "F" represent sequences selected from the group consisting of MDV-1 RNA, Q-beta RNA, microvariant RNA, midivariant RNA, nanovariant RNA or modifications thereof which permit sections A and F to be replicated.

14. A kit for determining the presence or absence of a first subunit protein component of the enzyme telomerase comprising a first ribonucleic acid (RNA) molecule and a second RNA molecule, ligase means and amplification means, said first RNA molecule which binds said first subunit protein component under binding conditions and has the following formula:

$$5'-A-B-C-3'$$

wherein A is a section of the RNA molecule having 10 to 100,000 nucleotides which section is, with another RNA sequence, F, replicated by an RNA replicase and the letter "B" denotes a section of the RNA molecule having approximately 10 to 250 nucleotides comprising sequences from the Y region of human telomerase, which section specifically binds said first subunit protein component under binding conditions, and the letter "C" denotes a section of the RNA molecule having approximately 1 to 10,000 nucleotides, which section is ligated to another RNA sequence, "D"; under ligating conditions said second RNA molecule which binds said first subunit protein component and has the following formula:

$$5'-D-E-F-3'$$

wherein D is a section of the RNA molecule having approximately 1 to 10,000 nucleotides which section is ligated to another RNA sequence, "C", under ligating conditions and the letter "E" denotes a section of the RNA molecule having approximately 10 to 250 nucleotides comprising sequences from the Y region of human telomerase which section specifically binds said first subunit protein component under binding conditions, and the letter "F" denotes a section of the RNA molecule having 10 to 100,000 nucleotides which section is, with another sequence, "A", replicated by an RNA replicase; said first and the second RNA molecules forming a third RNA molecule upon ligation having the following formula:

$$5'-A-B-C-D-E-F-3'$$

said third RNA molecule formed by ligating the C and D sections, as the E and the B sections are bound to said first subunit protein component, said third RNA molecule for being replicated by said RNA replicase as an indication of the presence or absence of said first subunit protein component; said ligase means for forming said third RNA molecule in the presence of said complex and said amplification means for forming a plurality of said third RNA molecules or corresponding RNA or DNA molecules in the presence of the said third molecule.

15. A method of making a first ribonucleic acid (RNA) molecule and a second RNA molecule for use in determining the presence or absence of the first subunit protein component of telomerase, said first RNA molecule which binds said first subunit protein component under binding conditions has the following formula:

$$5'-A-B-C-3'$$

wherein A is a section of the RNA molecule having 10–100,000 nucleotides which section is, with another RNA sequence, F, replicated by an RNA replicase under replicating conditions and the letter "B" denotes a section of the RNA molecule having approximately 10 to 250 nucleotides comprising sequences from the Y region of human telomerase which section specifically binds said first subunit protein component under binding conditions, and the letter "C" denotes a section of the RNA molecule having approximately 1 to 10,000 nucleotides which section is ligated to another RNA sequence, "D" under ligating conditions; said second RNA molecule which binds said first subunit protein component under binding conditions has the following formula:

$$5'-D-E-F-3'$$

wherein D is a section of the RNA molecule having approximately 1 to 10,000 nucleotides which section is ligated with another RNA sequence, "C", under ligating conditions and the letter "E" denotes a section of the RNA molecule having approximately 10 to 250 nucleotides comprising sequences from the Y region of human telomerase which section specifically binds said first subunit protein component under binding conditions, and the letter "F" denotes a section of the RNA molecule having 10 to 100,000 nucleotides which section is, with another sequence, "A", replicated under replicating conditions; said first and the second RNA molecules forming a third RNA molecule upon ligation of sections C and D having the following formula:

$$5'-A-B-C-D-E-F-3'$$

said third RNA molecule formed by ligating the C and D sections, as the E and the B sections are bound to said first subunit protein component, said third RNA molecule for being replicated by said RNA replicase as an indication of the presence or absence of said first subunit protein component; comprising the step of transcribing a DNA encoding at least one of the group consisting of the first RNA molecule and the second RNA molecule.

* * * * *